US007347996B1

(12) United States Patent
Degen et al.

(10) Patent No.: US 7,347,996 B1
(45) Date of Patent: Mar. 25, 2008

(54) AVIAN CYTOKINES, SUCH AS IL-12, COMPRISING A P40 AND/OR P35 SUBUNIT AND VACCINES

(75) Inventors: Wilhelmus Gerardus Johannes Degen, AS Doetinchem (NL); Virgil Elisabeth Joseph Caspar Schijns, KA Nijmegen (NL)

(73) Assignees: Intevert International B.V., Boxmeer (NL); UD Technology Corporation, Newark, DE (US)

( * ) Notice: Subject to any disclaimer, the term of this patent is extended or adjusted under 35 U.S.C. 154(b) by 455 days.

(21) Appl. No.: 10/464,630

(22) Filed: Jun. 17, 2003

Related U.S. Application Data

(60) Provisional application No. 60/391,662, filed on Jun. 26, 2002.

(51) Int. Cl.
*A61K 45/00* (2006.01)
*C07K 1/00* (2006.01)
*A01N 37/18* (2006.01)

(52) U.S. Cl. .......................... 424/85.2; 530/351; 514/2
(58) Field of Classification Search ..................... None
See application file for complete search history.

(56) References Cited

FOREIGN PATENT DOCUMENTS

WO     199713859      4/1997
WO     2003024354 A2  3/2003

OTHER PUBLICATIONS

Mickle, JE and Cutting GR. Genotype-phenotype relationships in cystic fibrosis. Med. Clin. North Am. 2000. vol. 84, No. 3, p. 597-607.*
Altschul, S.F., et al. (1997). Gapped BLAST and PSI-BLAST: a new generation of protein database search programs. Nucleic Acids Research, 25(17), 3389-3402.
Belke, G. et al. (1996). Induction and detection of mRNA, molecular cloning and sequencing of canine interleukin. Veterinary Immunology and Immunopathology, 54(153).
Berman, P.W., et al. (Nov. 4, 1983). Detection of Antibodies to Herpes Simplex Virus with a Continuous Cell Line Expressing Cloned Glycoprotein D. Science, New Series, 222(4623), 524-527.
Brinster, R.L. et al. (Mar. 4, 1982). Regulation of metallothionein-thymidine kinase fusion plasmids injected into mouse eggs. Nature, 296: 39-42.
Bush, K., et al. (1994). Molecular cloning of feline interleukin 12 p35 reveals the conservation of leucine-zipper motifs present in human and murine IL-12 p35. Molecular Immunology, 31(17), 1373-1374.
Carr, J.A. et al. (1999). The Role of Endogenous Interleukin-12 in Resistance to Murine Cytomegalovirus (MCMV) Infection and a Novel Action for Endogenous IL-12 p40. Journal of Interferon and Cytokine Research, 19:1145-1152.
de Goër de Herve, M. G. et al. (Apr. 21, 2001), Following direct CD40 activation, human primary microglial cells produce IL-12 p40 but not bioactive IL-12 p70. CYTOKINE, 14(2), 88-96.

Decken, K. et al. (Oct. 1998). Interleukin-12 is essential for a protective Th1 response in Mice infected with *Cryptococcus neoformans*. Infection and Immunity, 66(10), 4994-5000.
Ding, A.H. (Oct. 1, 1988). Release of reactive nitrogen intermediates and reactive oxygen intermediates from mouse peritoneal macrophages. The Journal of Immunology, 141(7), 2407-2412.
Elkins, K.L. et al. (Apr. 2002). In vivo clearance of an intracellular bacterium, *Francisella tularensis* LVS, is dependent on the p40 subunit of interleukin-12 (IL-12) but not on IL-12 p70. Infection and Immunity, 70(4), 1936-1948.
Foss, D.L. et al. (1997). Molecular cloning and mRNA expression of porcine interleukin-12. Veterinary Immunology and Immunopathology, 57: 121-134.
Gorman, C.M. et al. (Nov. 1982). The Rous sarcoma virus long terminal repeat is a strong promoter when introduced into a variety of eukaryotic cells by DNA-mediated transfection. Proceedings of the National Academy of Sciences, 79: 6777-6781.
Heinzel, F.P. et al. (May 1997). In vivo production and function of IL-12 p40 homodimers. The Journal of Immunology, 158:4381-4388.
Henikoff, S. et al. (Nov. 1992). Amino acid substitution matrices from protein blocks. Proceedings of the National Academy of Sciences, 89: 10915-10919.
Hilton, L. S. et al. (2002). The emerging role of avian cytokines as immunotherapeutics and vaccine adjuvants. Veterinary Immunology and Immunopathology, 85:119-128.
Hölscher, C. et al. (Dec. 2001). A protective and agonistic function of IL-12p40 in mycobacterial infection. The Journal of Immunology, 167:6957-6966.
Lehmann, J. et al. (Nov. 2001). IL-12p40-Dependent Agonistic Effects on the Development of Protective Innate and Adaptive Immunity Against Salmonella Enteritidis. The Journal of Immunology, 167:5304-5315.
Lipman, D. J. et al. (Mar. 22, 1985). Rapid and sensitive protein similarity searches. Science, 227:1435-1441.
Lowenthal, J. W. (2000). Avian cytokines-the natural approach to therapeutics. Developmental & Comparative Immunology, 24:355-365.
Mattner, F. et al. (Nov. 1997). Treatment with Homodimeric Interleukin-12 (IL-12) p40 Protects Mice from IL-12-Dependent Shock but not from tumor necrosis factor alpha-dependent shock. Infection and Immunity, 65(11), 4734-4737.
Mettenleiter, T. C. et al. (1990). A glycoprotein gX-B-galactosidase fusion gene as insertional marker for rapid identification of pseudorabies virus mutants. Journal of Virological Methods, 30:55-65.
Nagai, A. et al. (May 1991). Structural and functional conservation of histidinol dehydrogenase between plants and microbes. Proceedings of the National Academy of Sciences, 88:4133-4137.
Needleman, S. B. et al. (1970). A General Method Applicable to the Search for Similarities in the Amino Acid Sequence of Two Proteins. Journal Molecular Biology, 48:443-453.
Oppmann, B. et al. (Nov. 2000). Novel p19 protein engages IL-12p40 to form a cytokine, IL-23 with biological activities similar as well as distinct from IL-12. Immunity, 13:715-725.

(Continued)

*Primary Examiner*—Robert Landsman
*Assistant Examiner*—Bruce D. Hissong
(74) *Attorney, Agent, or Firm*—William M. Blackstone

(57) ABSTRACT

Embodiments of the present invention generally relate to novel avian cytokines, to DNA sequences encoding these novel cytokines and to their use in adjuvants for vaccine purposes.

4 Claims, 12 Drawing Sheets

OTHER PUBLICATIONS

Piccotti, J. R. et al. (Jan. 1997). Differential effects of IL-12 receptor blockade with IL-12 p40 homodimer on the induction of CD4+ and CD8+ IFN-γ-Producing Cells. The Journal of Immunology, 158:643-648.

Staeheli, P. et al. (2001). Cytokines of Birds: Conserved functions-a largely different look. Journal of Interferon and Cytokine Research. 21:993-1010.

Stuehr, D. J. et al. (May 1989). Nitric Oxide A macrophage product responsible for cytostasis and respiratory inhibition in tumor target cells. The Journal of Experimental Medicine, 169:1543-1555.

Trinchieri, G. (Dec. 15, 1994). Interleukin-12: A cytokine produced by antigen-presenting cells with immunoregulatory functions in the generation of t-helper cells type 1 and cytotoxic lymphocytes. Blood, 84(12), 4008-4027.

Voellmy, R. et al. (Aug. 1985). Isolation and functional analysis of a human 70,000-dalton heat shock protein gene segment. Proceednngs of the National Academy of Sciences, 82:4949-4953.

Wiekowski, M.T. et al. (2001). Ubiquitous transgenic expression of the IL-23 subunit p19 induces multiorgan inflammation, runting, infertility, and premature death. The Journal of Immunology, 166:7563-7570.

Wolf, S. F., et al. (May 1, 1991). Cloning of cDNA for natural killer cell stimulatory factor, a heterodimeric cytokine with multiple biologic effects on T and natural killer cells. The Journal of Immunology, 146(9), 3074-3081.

Yoshimoto, T. et al. (1996). Molecular cloning and characterization of murine IL-12 genes. The Journal of Immunology, 156:1082-1088.

Gately, M. K. et al. (1995). Measurement of Human and Mouse Interleukin-12. Current Protocols in Immunity, Supplement 15, Unit 6.16.

Dayhoff, Margaret O. (1978). Atlas of Protein Sequence and Structure. vol. 5:Supplement 3. Publisher: National Biomedical Research Foundation, Washington, DC.

Rodriguez, Raymond L. and Denhardt, David T., (Oct. 1987). VECTORS A Survey of Molecular Cloning Vectors and Their Uses. Publisher: Butterworth-Heinemann, Stoneham, MA.

Ausubel, Frederick M. (1989). Current protocols in molecular biology. Publisher: Greene Publishing Associates, Brooklyn, N.Y.

Glover, D.M. and Hames, B.D. (1996). DNA Cloning, vols. 1-4, edition 1995. Publisher: Oxford University Press, USA.

* cited by examiner

ChIL-12 p35 na + aa

```
     M  A  E  H  G  I  G  I  G  S  R  A  A  R  L  G  V  G  R  C
  1 ATGGCAGAGCACGGCATCGGCATCGGCAGCAGAGCGGCACGGCTGGGGGTCGGGCGCTGC  60

V  L  L  A  A  L  C  L  L  L  P  S  T  W  A  L  P  P  P  A
 61 GTGCTGCTGGCCGCGCTCTGCCTGCTGCTGCCTTCCACGTGGGCACTGCCACCTCCTGCC 120

H  N  L  A  K  G  L  N  C  S  R  A  L  L  A  A  A  N  E  A
121 CACAACCTGGCCAAGGGACTCAACTGCTCCAGGGCGCTGCTGGCCGCTGCAAACGAGGCA 180

L  L  K  V  Q  K  Q  R  T  L  G  F  E  C  T  L  E  E  V  D
181 CTCCTGAAGGTGCAGAAGCAGAGGACGCTGGGGTTTGAGTGCACCCTTGAAGAGGTCGAT 240

L  E  D  V  T  N  S  Q  S  N  T  I  K  S  C  T  S  Q  D  P
241 CTTGAAGACGTCACCAACAGTCAGAGCAACACAATAAAGTCCTGCACGTCTCAGGATCCG 300

G  P  G  N  C  P  V  L  E  S  S  T  L  D  M  S  K  C  L  Q
301 GGGCCTGGAAACTGCCCCGTACTGGAAAGTTCTACTTTAGATATGAGCAAATGCCTGCAG 360

G  I  Y  E  D  L  K  T  Y  K  A  E  L  G  N  L  K  D  L  R
361 GGGATCTACGAAGACCTGAAAACCTACAAGGCAGAGCTGGGGAACCTCAAGGATCTGAGG 420

V  L  T  S  I  D  D  M  M  Q  A  L  Q  P  R  S  P  A  M  P
421 GTGCTGACATCCATTGATGACATGATGCAAGCCCTGCAGCCCCGCAGCCCAGCCATGCCG 480

Q  P  S  P  S  T  T  L  G  S  F  Q  G  R  M  R  L  C  G  V
481 CAGCCCTCGCCCAGCACCACCCTTGGCTCCTTCCAGGGCCGCATGCGGCTCTGCGGGGTC 540

L  H  A  F  C  L  R  A  V  T  I  G  R  M  L  G  Y  L  S  A
541 CTGCACGCCTTCTGCCTGCGCGCAGTCACCATCGGCAGGATGCTGGGCTACCTGAGTGCC 600

L  T  A  E  M  *
601 CTCACTGCAGAGATGTAA 618
```

FIG. 1

ACCTGGACATATCCCAAGACCTGGAGCACA

ATCCTGGAGTGAGTGGTCCACGCTTTGCAGATAA

FIG. 2

ChIL-12 p40 DNA + aa

```
      M   S   H   L   L   F   A   L   L   S   L   L   S   F   A   A   L   L   E   A
  1 ATGTCTCACCTGCTATTTGCCTTACTTTCATTACTTTCCTTTGCTGCCCTTCTGGAAGCA  60

Q   W   K   L   R   E   N   V   Y   V   I   E   S   E   W   N   D   E   T   P
 61 CAGTGGAAACTTAGAGAGAATGTGTATGTCATAGAATCTGAGTGGAACGATGAGACACCA 120

A   K   K   V   K   L   T   C   D   T   S   D   E   A   L   P   V   Y   W   K
121 GCTAAAAAAGTGAAGCTCACCTGTGACACATCTGATGAAGCACTGCCAGTTTACTGGAAA 180

K   G   T   E   L   K   G   T   G   K   T   L   T   T   E   V   K   E   F   P
181 AAGGGAACAGAACTGAAAGGAACTGGAAAGACTCTGACCACCGAAGTGAAGGAGTTCCCA 240

D   A   G   N   Y   T   C   L   S   A   K   T   H   E   I   I   S   Y   S   F
241 GATGCTGGCAACTACACCTGCCTGTCTGCTAAGACCCACGAGATTATCAGCTACAGTTTC 300

F   L   I   T   K   V   D   S   N   G   Q   M   I   R   S   I   L   K   S   Y
301 TTTCTCATAACTAAAGTAGACTCCAATGGGCAAATGATACGGTCAATTCTGAAAAGCTAT 360

K   E   P   S   K   T   F   L   K   C   E   A   K   N   Y   S   G   I   F   T
361 AAAGAGCCAAGCAAGACGTTCTTAAAATGTGAGGCAAAGAACTACTCTGGAATTTTCACA 420

C   S   W   M   T   E   N   E   S   P   S   V   K   F   T   I   R   S   L   K
421 TGTTCATGGATGACAGAAAATGAGAGTCCAAGTGTGAAGTTCACAATTAGGAGCCTAAAA 480

G   S   Q   G   D   V   T   C   S   S   P   V   A   R   T   D   K   S   V   T
481 GGCTCTCAAGGAGATGTAACCTGCAGCAGCCCTGTGGCTCGCACTGATAAATCTGTGACT 540

E   Y   T   A   Q   C   Q   K   E   N   Y   C   P   F   A   E   E   H   Q   P
541 GAATACACTGCCCAGTGCCAGAAGGAAAACTACTGTCCATTTGCCGAAGAGCACCAGCCG 600

T   E   M   F   L   E   V   I   D   E   V   E   Y   E   N   Y   T   S   S   F
601 ACTGAGATGTTCCTGGAGGTCATTGATGAGGTGGAATATGAGAACTACACTAGTAGCTTC 660

F   I   R   D   I   I   K   P   D   P   P   Q   C   Q   Y   A   S   T   N   G
661 TTCATCAGAGATATCATAAAGCCAGACCCACCTCAATGTCAGTATGCAAGCACAAATGGA 720

T   V   T   W   T   Y   P   K   T   W   S   T   P   K   S   Y   F   P   L   T
721 ACTGTGACCTGGACATATCCCAAGACCTGGAGCACACCGAAGTCCTACTTCCCTTTGACT 780

F   R   V   K   V   E   S   T   K   K   Y   K   S   K   V   Y   D   A   D   E
781 TTCAGGGTCAAAGTTGAAAGCACAAAGAAATACAAAAGCAAGGTTTATGATGCTGATGAG 840

Q   S   I   Q   I   P   K   T   G   P   K   D   K   I   S   V   Q   A   R   D
841 CAGTCTATTCAGATTCCAAAGACTGGGCCAAAAGACAAGATCTCTGTGCAGGCCAGGGAT 900

R   Y   Y   N   S   S   W   S   E   W   S   T   L   C   R   *
901 CGCTATTACAACTCATCCTGGAGTGAGTGGTCCACGCTTTGCAGATAA 948
```

FIG. 3

Duck IL-12 p40 DNA + aa

```
      M   S   H   L   L   F   A   L   L   S   L   L   S   F   A   A   L   L   E   A
  1 ATGTCTCACCTGCTATTTGCCTTACTTTCATTACTTTCCTTTGCTGCCCTTCTGGAAGCA  60

Q   W   K   L   R   E   N   V   Y   V   I   E   S   E   W   N   D   E   T   P
 61 CAGTGGAAACTTAGAGAGAATGTGTATGTCATAGAATCTGAGTGGAACGATGAGACACCA 120

A   K   K   V   K   L   T   C   D   T   S   D   E   A   L   P   V   Y   W   K
121 GCTAAAAAAGTGAAGCTCACCTGTGACACATCTGATGAAGCACTGCCAGTTTACTGGAAA 180

K   G   T   E   L   K   G   T   G   K   T   L   T   T   E   V   K   E   F   P
181 AAGGGAACAGAACTGAAAGGAACCGGAAAGACTCTGACCACCGAAGTGAAGGAGTTCCCA 240

D   A   G   N   Y   T   C   L   S   A   K   T   H   E   I   I   S   Y   S   F
241 GATGCTGGCAACTACACCTGCCTGTCTGCTAAGACCCACGAGATTATCAGCTACAGTTTC 300

F   L   I   T   K   V   D   S   N   G   Q   M   I   R   S   I   L   K   S   Y
301 TTTCTCATAACTAAAGTAGACTCCAATGGGCAAATGATACGGTCAATCCTGAAAAGCTAT 360

K   E   P   S   K   T   F   L   K   C   E   A   K   N   Y   S   G   I   F   T
361 AAAGAGCCAAGCAAGACGTTCTTAAAATGTGAGGCAAAGAACTACTCTGGAATTTTCACA 420

C   S   W   M   T   E   N   E   S   P   S   V   K   F   T   I   R   S   L   K
421 TGTTCATGGATGACAGAAAATGAGAGTCCAAGTGTGAAGTTCACAATTAGGAGCCTAAAA 480

G   S   Q   G   D   V   T   C   S   S   P   V   A   R   T   D   K   S   V   T
481 GGCTCTCAAGGAGATGTAACCTGCAGCAGCCCTGTGGCTCGCACCGATAAATCTGTGACT 540

E   Y   T   A   Q   C   Q   K   E   N   Y   C   P   F   A   E   E   H   Q   P
541 GAATACACTGCCCAGTGCCAGAAGGAAAACTACTGTCCATTCGCCGAAGAGCACCAGCCG 600

T   E   M   F   L   E   V   I   D   E   V   E   Y   E   N   Y   T   S   S   F
601 ACTGAGATGTTCCTGGAGGTCATTGATGAGGTGGAATATGAGAACTACACTAGTAGCTTC 660

F   I   R   D   I   I   K   P   D   P   P   Q   C   Q   Y   A   S   T   N   G
661 TTCATCAGAGATATCATAAAGCCAGACCCACCTCAATGTCAGTATGCAAGCACAAATGGA 720

T   V   T   W   T   Y   P   K   T   W   S   T   P   K   S   Y   F   P   L   T
721 ACTGTGACCTGGACATATCCCAAGACCTGGAGCACACCGAAGTCCTACTTCCCTTTGACT 780

F   R   V   K   V   E   S   T   K   K   Y   K   S   K   V   Y   D   A   D   E
781 TTCAGGGTCAAAGTTGAAAGCACAAAGAAATACAAAAGCAAGGTTTATGATGCTGATGAG 840

Q   S   I   Q   I   P   K   T   G   P   K   D   K   I   S   V   Q   A   R   D
841 CAGTCTATTCAGATTCCAAAGACTGGGCCAAAAGACAAGATCTCTGTGCAGGCCAGGGAT 900

R   Y   Y   N   S   S   W   S   E   W   S   T   L   C   R   *
901 CGCTATTACAACTCATCCTGGAGTGAGTGGTCCACGCTTTGCAGATAA 948
```

FIG. 4

Turkey IL-12 p40 DNA + aa

```
      M   S   H   L   L   F   A   L   L   S   L   L   S   F   A   A   L   L   E   A
  1 ATGTCTCACCTGCTATTTGCCTTACTTTCATTACTTTCCTTTGCTGCCCTTCTGGAAGCA  60

Q   W   K   L   R   E   N   V   Y   V   I   E   S   E   W   N   D   E   T   P
 61 CAGTGGAAACTTAGAGAGAATGTGTATGTCATAGAATCTGAGTGGAACGATGAGACACCA 120

A   K   K   V   K   L   T   C   D   T   S   D   E   A   L   P   V   Y   W   K
121 GCTAAAAAAGTGAAGCTCACCTGTGACACATCTGATGAAGCACTGCCAGTTTACTGGAAA 180

K   G   T   E   L   K   G   T   G   K   T   L   T   T   E   V   K   E   F   P
181 AAGGGAACAGAACTGAAAGGAACTGGAAAGACTCTGACCACCGAAGTGAAGGAGTTCCCA 240

D   A   G   N   Y   T   C   L   S   A   K   T   H   E   I   I   S   Y   S   F
241 GATGCTGGCAACTACACCTGCCTGTCTGCTAAGACCCACGAGATTATCAGCTACAGTTTC 300

F   L   I   T   K   V   D   S   N   G   Q   M   I   R   S   I   L   K   S   Y
301 TTTCTCATAACTAAAGTAGACTCCAATGGGCAAATGATACGGTCAATTCTGAAAAGCTAT 360

K   E   P   S   K   T   F   S   K   C   E   A   K   N   Y   S   G   I   F   T
361 AAAGAGCCAAGCAAGACGTTCTCAAAATGTGAGGCAAAGAACTACTCTGGAATTTTCACA 420

C   S   W   M   T   E   N   E   S   P   S   V   K   F   T   I   R   S   L   K
421 TGTTCATGGATGACAGAAAATGAGAGTCCAAGTGTGAAGTTCACAATTAGGAGCCTAAAA 480

G   S   Q   G   D   V   T   C   S   S   P   V   A   R   T   D   K   S   V   T
481 GGCTCTCAAGGAGATGTAACCTGCAGCAGCCCTGTGGCTCGCACTGATAAATCTGTGACT 540

E   Y   T   A   Q   C   Q   K   E   N   Y   C   P   F   A   E   E   H   Q   P
541 GAATACACTGCCCAGTGCCAGAAGGAAAACTACTGTCCATTTGCCGAAGAGCACCAGCCG 600

T   E   M   F   L   E   V   I   D   E   V   E   Y   E   N   Y   T   S   S   F
601 ACTGAGATGTTCCTGGAGGTCATTGATGAGGTGGAATATGAGAACTACACTAGTAGCTTC 660

F   I   R   D   I   I   K   P   D   P   P   Q   C   Q   Y   A   S   T   N   G
661 TTCATCAGAGATATCATAAAGCCAGACCCACCTCAATGTCAGTATGCAAGCACAAATGGA 720

T   V   T   W   T   Y   P   K   T   W   S   T   P   K   S   Y   F   P   L   T
721 ACTGTGACCTGGACATATCCCAAGACCTGGAGCACACCGAAGTCCTACTTCCCTTTGACT 780

F   R   V   K   V   E   S   T   K   K   Y   K   S   K   V   Y   D   A   D   E
781 TTCAGGGTCAAAGTTGAAAGCACAAAGAAATACAAAAGCAAGGTTTATGATGCTGATGAG 840

Q   S   I   Q   I   P   K   T   G   P   K   D   K   I   S   V   Q   A   R   D
841 CAGTCTATTCAGATTCCAAAGACTGGGCCAAAAGACAAGATCTCTGTGCAGGCCAGGGAT 900

R   Y   Y   N   S   S   W   S   E   W   S   T   L   C   R   *
901 CGCTATTACAACTCATCCTGGAGTGAGTGGTCCACGCTTTGCAGATAA 948
```

IL-12 p40 protein multile alignment

```
            10         20         30         40         50         60         70         80         90        100        110        120
chicken MSHLLFALLSLLSFAALLEAQWKLRENVVIESEMNDKTPAKKVKLICZHSDEALPVYWKKGTELKGTGKTLTIEVKEFPDAGNYTCLSAKTHEIISYSYSFFLJTKVDSNGQMIRSILKSY 120
duck    ............................................................................................................ 120
turkey  ............................................................................................................ 120

130        140        150        160        170        180        190        200        210        220        230        240
chicken KEPSKTFLKCEARNYSGIFTCSMATENSSPSVKFTIRSLKGSQGDVTCSSPVARTDKSVTETAQCQKENYCPFABBHQPTEMFLEVIDEVEYENYISSFFIROIIKPDPPQCQYIASTNG 240
duck    .............................................................................................................. 240
turkey  ......S....................................................................................................... 240

250        260        270        280        290        300
chicken TVTWTYPKTWSTPRKSYFPLTFRVKVESTKKYKSKVTDADEQSIQIPKKUGPRDKISVQARDRYNSSMSEWSTLCR 315
duck    .......................................................................... 315
turkey  .......................................................................... 315
```

FIG. 7

SEQUENCE LISTING

```
<160> NUMBER OF SEQ ID NOS: 21

<210> SEQ ID NO 1
<211> LENGTH: 315
<212> TYPE: PRT
<213> ORGANISM: Chicken

<400> SEQUENCE: 1

Met Ser His Leu Leu Phe Ala Leu Leu Ser Leu Leu Ser Phe Ala Ala
1               5                   10                  15

Leu Leu Glu Ala Gln Trp Lys Leu Arg Glu Asn Val Tyr Val Ile Glu
            20                  25                  30

Ser Glu Trp Asn Asp Glu Thr Pro Ala Lys Lys Val Lys Leu Thr Cys
        35                  40                  45

Asp Thr Ser Asp Glu Ala Leu Pro Val Tyr Trp Lys Lys Gly Thr Glu
    50                  55                  60

Leu Lys Gly Thr Gly Lys Thr Leu Thr Thr Glu Val Lys Glu Phe Pro
65                  70                  75                  80

Asp Ala Gly Asn Tyr Thr Cys Leu Ser Ala Lys Thr His Glu Ile Ile
                85                  90                  95

Ser Tyr Ser Phe Phe Leu Ile Thr Lys Val Asp Ser Asn Gly Gln Met
            100                 105                 110

Ile Arg Ser Ile Leu Lys Ser Tyr Lys Glu Pro Ser Lys Thr Phe Leu
        115                 120                 125

Lys Cys Glu Ala Lys Asn Tyr Ser Gly Ile Phe Thr Cys Ser Trp Met
    130                 135                 140

Thr Glu Asn Glu Ser Pro Ser Val Lys Phe Thr Ile Arg Ser Leu Lys
145                 150                 155                 160

Gly Ser Gln Gly Asp Val Thr Cys Ser Ser Pro Val Ala Arg Thr Asp
                165                 170                 175

Lys Ser Val Thr Glu Tyr Thr Ala Gln Cys Gln Lys Glu Asn Tyr Cys
            180                 185                 190

Pro Phe Ala Glu Glu His Gln Pro Thr Glu Met Phe Leu Glu Val Ile
        195                 200                 205

Asp Glu Val Glu Tyr Glu Asn Tyr Thr Ser Ser Phe Phe Ile Arg Asp
    210                 215                 220

Ile Ile Lys Pro Asp Pro Gln Cys Gln Tyr Ala Ser Thr Asn Gly
225                 230                 235                 240

Thr Val Thr Trp Thr Tyr Pro Lys Thr Trp Ser Thr Pro Lys Ser Tyr
                245                 250                 255

Phe Pro Leu Thr Phe Arg Val Lys Val Glu Ser Thr Lys Lys Tyr Lys
```

```
                 260                 265                 270
Ser Lys Val Tyr Asp Ala Asp Glu Gln Ser Ile Gln Ile Pro Lys Thr
            275                 280                 285

Gly Pro Lys Asp Lys Ile Ser Val Gln Ala Arg Asp Arg Tyr Tyr Asn
            290                 295                 300

Ser Ser Trp Ser Glu Trp Ser Thr Leu Cys Arg
305                 310                 315

<210> SEQ ID NO 2
<211> LENGTH: 205
<212> TYPE: PRT
<213> ORGANISM: Chicken

<400> SEQUENCE: 2

Met Ala Glu His Gly Ile Gly Ile Gly Ser Arg Ala Ala Arg Leu Gly
1               5                   10                  15

Val Gly Arg Cys Val Leu Leu Ala Ala Leu Cys Leu Leu Leu Pro Ser
            20                  25                  30

Thr Trp Ala Leu Pro Pro Pro Ala His Asn Leu Ala Lys Gly Leu Asn
        35                  40                  45

Cys Ser Arg Ala Leu Leu Ala Ala Ala Asn Glu Ala Leu Leu Lys Val
50                  55                  60

Gln Lys Gln Arg Thr Leu Gly Phe Glu Cys Thr Leu Glu Glu Val Asp
65                  70                  75                  80

Leu Glu Asp Val Thr Asn Ser Gln Ser Asn Thr Ile Lys Ser Cys Thr
                85                  90                  95

Ser Gln Asp Pro Gly Pro Gly Asn Cys Pro Val Leu Glu Ser Ser Thr
            100                 105                 110

Leu Asp Met Ser Lys Cys Leu Gln Gly Ile Tyr Glu Asp Leu Lys Thr
        115                 120                 125

Tyr Lys Ala Glu Leu Gly Asn Leu Lys Asp Leu Arg Val Leu Thr Ser
    130                 135                 140

Ile Asp Asp Met Met Gln Ala Leu Gln Pro Arg Ser Pro Ala Met Pro
145                 150                 155                 160

Gln Pro Ser Pro Ser Thr Thr Leu Gly Ser Phe Gln Gly Arg Met Arg
                165                 170                 175

Leu Cys Gly Val Leu His Ala Phe Cys Leu Arg Ala Val Thr Ile Gly
            180                 185                 190

Arg Met Leu Gly Tyr Leu Ser Ala Leu Thr Ala Glu Met
        195                 200                 205

<210> SEQ ID NO 3
<211> LENGTH: 948
<212> TYPE: DNA
<213> ORGANISM: Chicken

<400> SEQUENCE: 3
atgtctcacc tgctatttgc cttactttca ttactttcct tgctgccct tctggaagca      60 cagtggaaac ttagagagaa tgtgtatgtc atagaatctg agtggaacga tgagacacca     120
gctaaaaaag tgaagctcac ctgtgacaca tctgatgaag cactgccagt ttactggaaa     180
aagggaacag aactgaaagg aactgaaaag actctgacca ccgaagtgaa ggagttccca     240
gatgctggca actacacctg cctgtctgct aagacccacg agattatcag ctacagtttc     300
tttctcataa ctaaagtaga ctccaatggg caaatgatac ggtcaattct gaaaagctat     360
aaagagccaa gcaagacgtt cttaaaatgt gaggcaaaga actactctgg aattttcaca     420
```

-continued

```
tgttcatgga tgacagaaaa tgagagtcca agtgtgaagt tcacaattag agcctaaaa      480
ggctctcaag gagatgtaac ctgcagcagc cctgtggctc gcactgataa atctgtgact    540
gaatacactg cccagtgcca gaaggaaaac tactgtccat tgccgaaga gcaccagccg     600
actgagatgt tcctggaggt cattgatgag gtggaatatg agaactacac tagtagcttc    660
ttcatcagag atatcataaa gccagaccca cctcaatgtc agtatgcaag cacaaatgga   720
actgtgacct ggacatatcc caagacctgg agcacaccga agtcctactt cccttttgact  780
ttcagggtca agttgaaag cacaaagaaa tacaaaagca aggtttatga tgctgatgag    840
cagtctattc agattccaaa gactgggcca aaagacaaga tctctgtgca ggccagggat   900
cgctattaca actcatcctg gagtgagtgg tccacgcttt gcagataa                 948

<210> SEQ ID NO 4
<211> LENGTH: 618
<212> TYPE: DNA
<213> ORGANISM: Chicken

<400> SEQUENCE: 4
atggcagagc acggcatcgg catcggcagc agagcggcac ggctgggggt cgggcgctgc    60
gtgctgctgg ccgcgctctg cctgctgctg ccttccacgt gggcactgcc acctcctgcc   120
cacaacctgg ccaagggact caactgctcc agggcgctgc tggccgctgc aaacgaggca   180
ctcctgaagg tgcagaagca gaggacgctg gggtttgagt gcacccttga agaggtcgat   240
cttgaagacg tcaccaacag tcagagcaac acaataaagt cctgcacgtc tcaggatccg   300
gggcctggaa actgccccgt actggaaagt tctactttag atatgagcaa atgcctgcag   360
gggatctacg aagacctgaa aacctacaag gcagagctgg ggaaccctcaa ggatctgagg   420
gtgctgacat ccattgatga catgatgcaa gccctgcagc ccgcagccc agccatgccg    480
cagccctcgc ccagcaccac ccttggctcc ttccagggcc gcatgcgggct ctgcggggtc   540
ctgcacgcct tctgcctgcg cgcagtcacc atcggcagga tgctgggcta cctgagtgcc   600
ctcactgcag agatgtaa                                                  618

<210> SEQ ID NO 5
<211> LENGTH: 315
<212> TYPE: PRT
<213> ORGANISM: Duck

<400> SEQUENCE: 5

Met Ser His Leu Leu Phe Ala Leu Leu Ser Leu Leu Ser Phe Ala Ala
1               5                   10                  15

Leu Leu Glu Ala Gln Trp Lys Leu Arg Glu Asn Val Tyr Val Ile Glu
            20                  25                  30

Ser Glu Trp Asn Asp Glu Thr Pro Ala Lys Lys Val Lys Leu Thr Cys
        35                  40                  45

Asp Thr Ser Asp Glu Ala Leu Pro Val Tyr Trp Lys Lys Gly Thr Glu
    50                  55                  60

Leu Lys Gly Thr Gly Lys Thr Leu Thr Glu Val Lys Glu Phe Pro
65                  70                  75                  80

Asp Ala Gly Asn Tyr Thr Cys Leu Ser Ala Lys Thr His Glu Ile Ile
            85                  90                  95

Ser Tyr Ser Phe Phe Leu Ile Thr Lys Val Asp Ser Asn Gly Gln Met
        100                 105                 110

Ile Arg Ser Ile Leu Lys Ser Tyr Lys Glu Pro Ser Lys Thr Phe Ser
```

```
                    115                 120                 125
Lys Cys Glu Ala Lys Asn Tyr Ser Gly Ile Phe Thr Cys Ser Trp Met
    130                 135                 140

Thr Glu Asn Glu Ser Pro Ser Val Lys Phe Thr Ile Arg Ser Leu Lys
145                 150                 155                 160

Gly Ser Gln Gly Asp Val Thr Cys Ser Ser Pro Val Ala Arg Thr Asp
                165                 170                 175

Lys Ser Val Thr Glu Tyr Thr Ala Gln Cys Gln Lys Glu Asn Tyr Cys
                180                 185                 190

Pro Phe Ala Glu Glu His Gln Pro Thr Glu Met Phe Leu Glu Val Ile
                195                 200                 205

Asp Glu Val Glu Tyr Glu Asn Tyr Thr Ser Ser Phe Phe Ile Arg Asp
                210                 215                 220

Ile Ile Lys Pro Asp Pro Pro Gln Cys Gln Tyr Ala Ser Thr Asn Gly
225                 230                 235                 240

Thr Val Thr Trp Thr Tyr Pro Lys Thr Trp Ser Thr Pro Lys Ser Tyr
                245                 250                 255

Phe Pro Leu Thr Phe Arg Val Lys Val Glu Ser Thr Lys Lys Tyr Lys
                260                 265                 270

Ser Lys Val Tyr Asp Ala Asp Glu Gln Ser Ile Gln Ile Pro Lys Thr
                275                 280                 285

Gly Pro Lys Asp Lys Ile Ser Val Gln Ala Arg Asp Arg Tyr Tyr Asn
                290                 295                 300

Ser Ser Trp Ser Glu Trp Ser Thr Leu Cys Arg
305                 310                 315

<210> SEQ ID NO 6
<211> LENGTH: 948
<212> TYPE: DNA
<213> ORGANISM: Duck

<400> SEQUENCE: 6
atgtctcacc tgctatttgc cttactttca ttactttcct ttgctgccct tctggaagca      60
cagtggaaac ttagagagaa tgtgtatgtc atagaatctg agtggaacga tgagacacca     120
gctaaaaaag tgaagctcac ctgtgacaca tctgatgaag cactgccagt ttactggaaa     180
aagggaacag aactgaaagg aaccggaaag actctgacca ccgaagtgaa ggagttccca     240
gatgctggca actacacctg cctgtctgct aagacccacg agattatcag ctacagtttc     300
tttctcataa ctaaagtaga ctccaatggg caaatgatac ggtcaatcct gaaaagctat     360
aaagagccaa gcaagacgtt ctcaaaatgt gaggcaaaga actactctgg aattttcaca     420
tgttcatgga tgacagaaaa tgagagtcca agtgtgaagt tcacaattag agcctaaaa     480 ggctctcaag gagatgtaac ctgcagcagc cctgtggctc gcaccgataa atctgtgact     540
gaatacactg cccagtgcca gaggaaaaac tactgtccat tcgccgaaga gcaccagccg     600
actgagatgt tcctggaggt cattgatgag gtggaatatg agaactacac tagtagcttc     660
ttcatcagag atatcataaa gccagaccca cctcaatgtc agtatgcaag cacaaatgga     720
actgtgacct ggacatatcc caagacctgg agcacaccga gtcctacttc cctttgact      780 ttcagggtca aagttgaaag cacaaagaaa tacaaaagca aggtttatga tgctgatgag     840
cagtctattc agattccaaa gactgggcca aaagacaaga tctctgtgca ggccagggat     900
cgctattaca actcatcctg gagtgagtgg tccacgcttt gcagataa                  948
```

<210> SEQ ID NO 7
<211> LENGTH: 315
<212> TYPE: PRT
<213> ORGANISM: Turkey

<400> SEQUENCE: 7

```
Met Ser His Leu Leu Phe Ala Leu Leu Ser Leu Leu Ser Phe Ala Ala
1               5                   10                  15

Leu Leu Glu Ala Gln Trp Lys Leu Arg Glu Asn Val Tyr Val Ile Glu
            20                  25                  30

Ser Glu Trp Asn Asp Glu Thr Pro Ala Lys Lys Val Lys Leu Thr Cys
        35                  40                  45

Asp Thr Ser Asp Glu Ala Leu Pro Val Tyr Trp Lys Lys Gly Thr Glu
    50                  55                  60

Leu Lys Gly Thr Gly Lys Thr Leu Thr Thr Glu Val Lys Glu Phe Pro
65                  70                  75                  80

Asp Ala Gly Asn Tyr Thr Cys Leu Ser Ala Lys Thr His Glu Ile Ile
                85                  90                  95

Ser Tyr Ser Phe Phe Leu Ile Thr Lys Val Asp Ser Asn Gly Gln Met
            100                 105                 110

Ile Arg Ser Ile Leu Lys Ser Tyr Lys Glu Pro Ser Lys Thr Phe Ser
        115                 120                 125

Lys Cys Glu Ala Lys Asn Tyr Ser Gly Ile Phe Thr Cys Ser Trp Met
    130                 135                 140

Thr Glu Asn Glu Ser Pro Ser Val Lys Phe Thr Ile Arg Ser Leu Lys
145                 150                 155                 160

Gly Ser Gln Gly Asp Val Thr Cys Ser Ser Pro Val Ala Arg Thr Asp
                165                 170                 175

Lys Ser Val Thr Glu Tyr Thr Ala Gln Cys Gln Lys Glu Asn Tyr Cys
            180                 185                 190

Pro Phe Ala Glu Glu His Gln Pro Thr Glu Met Phe Leu Glu Val Ile
        195                 200                 205

Asp Glu Val Glu Tyr Glu Asn Tyr Thr Ser Ser Phe Phe Ile Arg Asp
    210                 215                 220

Ile Ile Lys Pro Asp Pro Gln Cys Gln Tyr Ala Ser Thr Asn Gly
225                 230                 235                 240

Thr Val Thr Cys Thr Tyr Pro Lys Thr Trp Ser Thr Pro Lys Ser Tyr
                245                 250                 255

Phe Pro Leu Thr Phe Arg Val Lys Val Glu Ser Thr Lys Lys Tyr Lys
            260                 265                 270

Ser Lys Val Tyr Asp Ala Asp Glu Gln Ser Ile Gln Ile Pro Lys Thr
        275                 280                 285

Gly Pro Lys Asp Lys Ile Ser Val Gln Ala Arg Asp Arg Tyr Tyr Asn
    290                 295                 300

Ser Ser Trp Ser Glu Trp Ser Thr Leu Cys Arg
305                 310                 315
```

<210> SEQ ID NO 8
<211> LENGTH: 948
<212> TYPE: DNA
<213> ORGANISM: Turkey

<400> SEQUENCE: 8

```
atgtctcacc tgctatttgc cttactttca ttactttcct tgctgccct tctggaagca      60 cagtggaaac ttagagagaa tgtgtatgtc atagaatctg agtggaacga tgagacacca     120
```

-continued

```
gctaaaaaag tgaagctcac ctgtgacaca tctgatgaag cactgccagt ttactggaaa      180
aagggaacag aactgaaagg aactggaaag actctgacca ccgaagtgaa ggagttccca      240
gatgctggca actacacctg cctgtctgct aagacccacg agattatcag ctacagtttc      300
tttctcataa ctaaagtaga ctccaatggg caaatgatac ggtcaattct gaaaagctat      360
aaagagccaa gcaagacgtt ctcaaaatgt gaggcaaaga actactctgg aattttcaca      420
tgttcatgga tgacagaaaa tgagagtcca agtgtgaagt tcacaattag gagcctaaaa      480
ggctctcaag gagatgtaac ctgcagcagc cctgtggctc gcactgataa atctgtgact      540
gaatacactg cccagtgcca gaggaaaaac tactgtccat tgccgaaga gcaccagccg      600 actgagatgt tcctggaggt cattgatgag gtggaatatg agaactacac tagtagcttc      660
ttcatcagag atatcataaa gccagaccca cctcaatgtc agtatgcaag cacaaatgga      720
actgtgacct gcacatatcc caagacctgg agcacaccga agtcctactt cccttttgact      780 ttcagggtca aagttgaaag cacaaagaaa tacaaaagca aggtttatga tgctgatgag      840
cagtctattc agattccaaa gactgggcca aaagacaaga tctctgtgca ggccagggat      900
cgctattaca actcatcctg gagtgagtgg tccacgcttt gcagataa                  948
```

<210> SEQ ID NO 9
<211> LENGTH: 40
<212> TYPE: DNA
<213> ORGANISM: Artificial
<220> FEATURE:
<223> OTHER INFORMATION: PCR and/or sequencing primer
<400> SEQUENCE: 9

```
ttggatccgg tggcggcgga tctctgccac ctcctgccca                            40
```

<210> SEQ ID NO 10
<211> LENGTH: 40
<212> TYPE: DNA
<213> ORGANISM: Artificial
<220> FEATURE:
<223> OTHER INFORMATION: PCR and/or sequencing primer
<400> SEQUENCE: 10

```
ccaagctttt acatctctgc agtgagggca ctcaggtagc                            40
```

<210> SEQ ID NO 11
<211> LENGTH: 40
<212> TYPE: DNA
<213> ORGANISM: Artificial
<220> FEATURE:
<223> OTHER INFORMATION: PCR and/or sequencing primer
<400> SEQUENCE: 11

```
ttgcggccgc catgtctcac ctgctatttg ccttactttc                            40
```

<210> SEQ ID NO 12
<211> LENGTH: 45
<212> TYPE: DNA
<213> ORGANISM: Artificial
<220> FEATURE:
<223> OTHER INFORMATION: PCR and/or sequencing primer
<400> SEQUENCE: 12

```
tggatccacc accgcccgag ccaccgccac ctctgcaaag cgtgg                      45
```

<210> SEQ ID NO 13
<211> LENGTH: 29

```
<212> TYPE: DNA
<213> ORGANISM: Artificial
<220> FEATURE:
<223> OTHER INFORMATION: PCR and/or sequencing primer

<400> SEQUENCE: 13
atgtgtcacc agyrgttggt cmtctcytg                              29

<210> SEQ ID NO 14
<211> LENGTH: 29
<212> TYPE: DNA
<213> ORGANISM: Artificial
<220> FEATURE:
<223> OTHER INFORMATION: PCR and/or sequencing primer

<400> SEQUENCE: 14
atgtgtcytc agmagytrry catctcctg                              29

<210> SEQ ID NO 15
<211> LENGTH: 29
<212> TYPE: DNA
<213> ORGANISM: Artificial
<220> FEATURE:
<223> OTHER INFORMATION: PCR and/or sequencing primer

<400> SEQUENCE: 15
atgtgtcwyc agyrgttggt cmtctcctg                              29

<210> SEQ ID NO 16
<211> LENGTH: 29
<212> TYPE: DNA
<213> ORGANISM: Artificial
<220> FEATURE:
<223> OTHER INFORMATION: PCR and/or sequencing primer

<400> SEQUENCE: 16
atgcaccctc agcagttggt cgtttcctg                              29

<210> SEQ ID NO 17
<211> LENGTH: 34
<212> TYPE: DNA
<213> ORGANISM: Artificial
<220> FEATURE:
<223> OTHER INFORMATION: PCR and/or sequencing primer

<400> SEQUENCE: 17
ttatctgcaa agcgtggacc actcactcca ggat                        34

<210> SEQ ID NO 18
<211> LENGTH: 30
<212> TYPE: DNA
<213> ORGANISM: Artificial
<220> FEATURE:
<223> OTHER INFORMATION: PCR and/or sequencing primer

<400> SEQUENCE: 18
acctggacat atcccaagac ctggagcaca                             30

<210> SEQ ID NO 19
<211> LENGTH: 34
<212> TYPE: DNA
<213> ORGANISM: Artificial
<220> FEATURE:
<223> OTHER INFORMATION: PCR and/or sequencing primer

<400> SEQUENCE: 19
```

-continued

```
ctggctaact agagaaccca ctgcttactg gctt                              34

<210> SEQ ID NO 20
<211> LENGTH: 20
<212> TYPE: DNA
<213> ORGANISM: Artificial
<220> FEATURE:
<223> OTHER INFORMATION: PCR and/or sequencing primer

<400> SEQUENCE: 20
atgtctcacc tgctatttgc                                              20

<210> SEQ ID NO 21
<211> LENGTH: 23
<212> TYPE: DNA
<213> ORGANISM: Artificial
<220> FEATURE:
<223> OTHER INFORMATION: PCR and/or sequencing primer

<400> SEQUENCE: 21
ttatctgcaa agcgtggacc act                                          23
```

AVIAN CYTOKINES, SUCH AS IL-12, COMPRISING A P40 AND/OR P35 SUBUNIT AND VACCINES

RELATED APPLICATION

This application claims priority to provisional application Ser. No. 60/391,662 filed Jun. 26, 2002.

REFERENCE TO SEQUENCE LISTING

The material saved as "text document" under the file name "Substitute Sequence Listing" created on Apr. 4, 2007 is hereby incorporated by reference.

FIELD OF THE INVENTION

The present invention relates to novel avian cytokines, to DNA sequences encoding these novel cytokines and to their use in adjuvants for vaccine purposes.

BACKGROUND OF THE INVENTION

The group of soluble secreted molecules, collectively termed cytokines, represents critical communication signals among the cells of the immune system and between immune and non-immune system cells. Some of these cytokines have to form homodimers, such as interferon-gamma (IFN-γ), or homotrimers, such as tumor necrosis factor (TNF)-family molecules, in order to exert biological activity. Monomeric forms show minimal or no bioactivity.

Cytokines are at present used in drugs in cancer therapy and in the combat against chronic microbial infections. Cytokines are also evaluated for their use as immune stimulators in adjuvants to improve vaccines.

In mammals, a group of composite hetero-dimeric cytokines has been identified based on complexes of a p40 protein subunit. The mammalian p40 element comprises a 40 kD protein which links covalently, by di-sulfide binding, with a p35 subunit to form interleukin-12 (IL-12) p70 (Gubler U, et al., PNAS USA 1991, 88: 4143-4147; Wolf S F, et al., J. Immunol. 1991, 146: 3047-3081; Trinchieri G., Blood 1994, 12: 4008-4027). In addition, p40 may form the composite cytokine IL-23, after combining with p19 (Wiekowski M T, et al., J. Immunol. 2001 166: 7563-7570), a molecule structurally related to IL-6, p35 and granulocyte-colony stimulating factor (G-CSF) (Oppmann B, et al., Immunity 2000, 13: 715-725). Moreover, p40 may form homodimers that have been shown to either compete for binding with IL-12 p70 to the IL-12 high affinity receptor and inhibit IL-12 bioactivity (Heinzel F P, et al., J. Immunol., 1997, 158: 4381-4388), or to enhance, rather than to decrease, IFN-γ production by CD8+ T cells and Th1 development (Piccotti J R, et al., J. Immunol. 1997, 158: 643-648).

The significance of p40 in vivo in various mammalian species has been demonstrated using recombinant p40. IL-12 antagonistic features of 80 KDa homodimeric $(P40)_2$ have been clearly demonstrated in lipopolysaccharide (LPS)-induced IFN-γ-dependent lethal shock models (Mattner F, et al., Infect. Immun. 1997, 11: 4734-4737). The production of human p40, in the absence of bioactive IL-12 p70, has been demonstrated for brain microglial cells (De Goer-de Herve M G, et al., Cytokine 2001, 14: 88-96). In addition, the physiological role of mammalian p40 composite cytokines has been delineated in detail using in vivo gene-targeting approaches. It proved that following infection by *Salmonella enteritidis* mice genetically deficient for the p40 protein (p40−/−) showed a higher mortality rate and higher bacterial organ burden than mice capable of producing p40, but lacking the p35 gene (IL-12 p35−/−) (Lehmann J, et al., J. Immunol. 2001, 167: 5304-5315). Normal (wild-type) and IL-12 p35−/− mice cleared an infection with *Mycobacterium bovis* Calmette-Guerin (BCG) or pulmonary tuberculosis infection, while double-deficient IL-12 (p35−/−+p40−/−) mice showed high susceptibility to *M. bovis* BCG and tuberculosis infection (Holscher C, et al., J. Immunol. 2001, 167: 6957-6566). Susceptibility was associated with reduced antigen-specific Th1 and cytotoxic T cell responses. Interestingly, in vivo therapy with recombinant p40 homodimers reverted *M. bovis* BCG infected double-depleted (p35−/−+p40−/−) mice into a resistant phenotype. This demonstrates a protective and agonistic role of endogenous and exogenous p40 in mycobacterial infection, which is independent of IL-12 p70 (Holscher et al., 2001 supra). Similarly, *Cryptococcus neoformans* infected p40−/− mice died earlier and developed higher organ burdens than p35−/− mice, which suggests again a protective role for the p40 subunit independent of the IL-12 heterodimer (Decken K., et al., Infect. Immunity 1998, 66: 4994-5000). Also, p40−/− mice survived large doses of the intracellular bacterium *Franscisella tularensis* (LVS), but never cleared bacteria and developed chronic infection. In sharp contrast, p35−/− mice readily survived large doses of sub lethal LVS infection. This study suggests that clearance of LVS is dependent on p40 but not on IL-12 p70 (Elkins K L, et al., Infect. Immun. 2002, 70: 1936-1946). Also during murine cytomegalovirus (MCMV) infection p35−/− mice showed an altered phenotype compared to p40−/− mice, indicating that p40 may have an activity independent of and additional to IL-12 antagonism in vivo (Carr J A, et al., J. Interferon Cytokine Res. 1999, 19: 1145-1152).

Taken together, these experimental studies illustrate the crucial role in mammals of p40 based cytokines such as IL-12, IL-23 and $(p40)_2$ in regulation of IFN-γ characteristic T helper-1 type immune responses essential in the control of mostly intracellular infections of bacterial, parasitic, fungal or viral nature.

The present invention concerns avian equivalents of the mammalian p40 based cytokines.

The cloning and sequencing of avian cytokines lags behind similar work done in mammals. Only a few avian cytokines have been identified so far. IFN-γ and IL-18 as well as a number of pro-inflammatory cytokines have been cloned, demonstrating the existence of a Th1-like cytokine network in chickens. Because of the low sequence homology to mammalian cytokines, usually somewhere around 30 to 50%, classical approaches to identify avian homologues of mammalian cytokines are usually not successful. The identification by PCR amplification using primers based on mammalian sequences is very difficult and unpredictive. (Hilton L. S. et al. Vet. Immunol. and Immunopathol. 2002, 85: 119-128; Staehi P. et al., J. Interferon Cytokine Res. 2001, 21: 993-1010) When some avian cytokines became available, work started to investigate their potential use as immune modulators or as immune adjuvants to enhance the efficiency of vaccines.

Most chickens produced in developed countries, both for consumption and egg-laying, are vaccinated. They are vaccinated against Marek's disease, and against Newcastle Disease Virus, Infectious Bursal Disease Virus, Infectious Bronchitis Virus, Fowlpox Virus, and Coccidial vaccines. Vaccination can be performed either before or after hatching. The immune systems of embryos and newly hatched birds is not yet fully developed and cannot give rise to an immune response that is as effective as 2-3 weeks after hatching. For the development of vaccines used pre-hatching or at-hatching, therefore a need exists for agents that enhance the immune response in birds after vaccination.

The present inventors have succeeded in identifying and determining both the amino acid- and the encoding gene sequence for novel avian cytokines. These proteins are useful for the above-mentioned purposes known for the mammalian counterparts, especially to enhance the effectiveness of avian vaccines.

SUMMARY OF THE INVENTION

The present invention provides a protein comprising at least one of the following polypeptide subunits:
a subunit having an amino acid sequence showing at least 80% similarity with the amino acid sequence as depicted in SEQ ID NO 1,
a subunit having an amino acid sequence showing at least 80% similarity with the amino acid sequence as depicted in SEQ ID NO 2.

DETAILED DESCRIPTION OF THE INVENTION

The sequence depicted in SEQ ID NO 1 represents a polypeptide having a molecular weight of approximately 40 kD. The sequence depicted in SEQ ID NO 2 represents a polypeptide having a molecular weight of approximately 35 kD.

The polypeptide subunit having a molecular weight of 40 kD will be referred to as "p40", while the 35 kD subunit will be referred to as "p35". Both sequences as depicted in SEQ ID NO 1 and 2 are derived from chicken DNA (chicken p40 and chicken p35).

As explained above for the mammalian cytokines, various p40 containing complexes may exist. p40 can appear as monomeric molecule, as homodimers, or as hetero-dimeric molecules. The p40 subunit, may be linked covalently, by di-sulfide binding, with the p35 subunit to form interleukin-12 (IL-12). In addition, p40 may form the composite cytokine IL-23, after combining with p19. The promiscuous binding of p40 to other cytokine peptide chains suggests the existence of hitherto other un-identified p40-complexing cytokines.

The proteins according to the invention may therefore be proteins consisting of one copy of one of the subunits, it may be homo-dimers of one of the subunits, especially p40, or a hetero-dimers consisting of one of the subunits (p40 or p35) together with another peptide subunit, or it may comprise both (p40 and p35) subunits. The invention also encompasses chimeric proteins comprising, for example, a chicken p40 or p35 subunit in combination with a p35 or p40 subunit derived from another species. Chimeras may be, for example, proteins wherein the chicken p35 is combined with a p40 derived from another avian or even non-avian species.

Together the p40 and p35, when linked by, for example, disulfide bonds, will form an avian Interleukin-12 (IL-12) which is likewise part of the present invention.

The proteins of the invention are in principle avian cytokines that can be used for different purposes, analogous to the mammalian counterparts. The cytokines according to the invention, especially the avian IL-12, more in particular the chicken IL-12, may be used as an adjuvant in avian vaccines to enhance the immune response.

Since it is obvious that minor modifications in the sequence of the protein are equally useful, the invention also provides for a protein comprising a polypeptide sub-unit having an amino acid sequence which has at least 80%, or preferably at least 90%, more preferably 95%, more preferably at least 99%, even most preferably 100% similarity to the sequence in SEQ ID NO 1 or SEQ ID NO 2.

The term "similarity" refers to a degree of similarity between proteins in view of differences in amino acids, but which different amino acids are functionally similar in view of almost equal size, lipophilicity, acidity etc. A percent similarity can be calculated by optimal alignment of the sequences using a similarity scoring matrix such as the Blosum62 matrix described in Henikoff S. and Henikoff J G., P. N. A. S. USA 1992, 89: 10915-10919. Calculation of the percentage similarity and optimal alignment of two sequences using the Blosum62 similarity matrix and the algorithm of Needleman and Wunsch (J. Mol. Biol. 1970, 48: 443-453) can be performed using the GAP program of the Genetics Computer Group (GCG, Madison, Wis., USA) using the default parameters of the program.

It is a further aspect of the invention to provide a protein which comprises a naturally occurring variant of one or both of the sub-units having the sequence as in SEQ ID NO 1 and SEQ ID NO 2. Such proteins, comprising a sub-unit having an amino acid sequence which has at least 80% similarity, preferably at least 90%, more preferably at least 95%, even more preferably at least 99% and most preferably 100% similarity to the polypeptides defined in SEQ ID NO 1 or SEQ ID NO 2, are derived from avian species such as chicken, duck, goose turkey and pigeon.

Such sequences are presented in SEQ ID NO 5 and 7, which represent the duck and turkey equivalent respectively of the chicken p40 amino acid sequence depicted in SEQ ID NO 1.

Such polymorphic forms and avian species homologues are included in the class of proteins made available by this invention. Variants of the proteins that are likewise part of the present invention can be natural variants that may contain variations in the amino acid sequence due to deletions, substitutions, insertions, inversions or additions of (an) amino acid(s) in said sequence. Amino acid substitutions that are expected not to essentially alter biological and immunological activities have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, 5: suppl. 3). Based on this information Lipman and Pearson developed a method for rapid and sensitive protein comparison and determination of the functional similarity between homologous polypeptides (Science 1985, 227: 1435-1441).

Other variants can be, for example, functional variants like salts, amides, esters, and specifically C-terminal esters, and N-acyl derivatives. Also included are peptides which are modified in vivo or in vitro, for example by glycosylation, amidation, carboxylation or phosphorylation.

Proteins comprising only a functional fragment of the p40 or p35 sub-unit (or both) are likewise considered as part of the present invention. A functional fragment of the polypeptide is a fragment that at least represents the part(s) of the polypeptide sub-unit(s), which is/are essential for the protein to be able to serve as a cytokine, and can fulfill this function, for example, when used alone or fused to heterologous sequences. Thus, such functional fragments, may be polypeptides that are functional per se, or the fragments may be functional when linked to other polypeptides, to obtain chimeric proteins. These functional fragments are understood to fall within the definition of the subunits.

Fragments can inter alia be produced by enzymatic cleavage of precursor molecules, using restriction endonucleases for the DNA and proteases for the polypeptides. Other methods include chemical synthesis of the fragments or the expression of peptide fragments by DNA fragments.

The polypeptide subunits have an apparent molecular weight of 40 or 35 kD respectively, based on the length of the amino acid (aa) sequence. The exact molecular weight can be determined in SDS-PAGE using reducing conditions.

Preferred proteins according to the invention are those proteins that comprise a polypeptide subunit having an amino acid sequence showing at least 80% similarity, preferably at least 90%, more preferably at least 95%, even more preferably at least 99% and most preferably 100% similarity to the protein defined in SEQ ID NO 1. Such preferred proteins according to the invention may comprise one or two p40 subunits (i.e. be a mono- or dimer of p40). Within this preferred embodiment most preferred are the proteins comprising a p40 subunit derived from chicken. Examples of subunits having over 99% similarity to the chicken sequence of SEQ ID NO 1 are the duck and turkey p40 sequences depicted in SEQ ID NO 5 and 7 respectively.

Especially useful are those proteins wherein the p40 subunit is linked to a p35 subunit (by a disulfide linkage) such that an avian IL-12 is obtained.

In an especially preferred embodiment the invention provides the chicken IL-12, consisting of a p40 subunit having the amino acid sequence of SEQ ID NO 1 and a p35 subunit having the amino acid sequence depicted in SEQ ID NO 2, linked together, for example, by a disulfide bond.

The linkage of the p35 and p40 subunits can be established in various ways. Chicken IL-12 can be generated via expression vectors containing both the p35 and p40 cDNAs separated by, for example, an IRES (internal ribosome entry segment) element or directly linked via a Glycine/Serine-rich coding region ("hinge") to form a single open reading frame. In addition, expression vectors containing either the p35 or p40 cDNA sequence under control of separate promoters can be used to generate chicken IL-12.

The preparation of the proteins, sub units or functional fragments thereof according to the invention is effected by means of one of the known organic chemical methods for peptide synthesis or with the aid of recombinant DNA techniques. This latter method involves the preparation of the desired peptide by means of expression using a recombinant polynucleotide with a nucleotide sequence, which is coding for one or more of the peptides in question in a suitable micro-organism as host.

These polynucleotides are likewise part of the present invention.

Thus the present invention furthermore provides a polynucleotide encoding at least one of the following polypeptide subunits:
  a subunit having an amino acid sequence having at least 80% similarity to the amino acid sequence as depicted in SEQ ID NO 1, and
  a subunit having an amino acid sequence having at least 80% similarity to the amino acid sequence as depicted in SEQ ID NO 2.

A polynucleotide encoding an avian IL-12 may comprise both sequences, for example, linked by a sequence encoding a hinge.

Fragments of the provided nucleic acid (na) sequence that encode a functional fragment of the polypeptide are likewise part of the present invention.

For example, a polynucleotide encoding such a functional fragment of the polypeptide may be fused to polynucleotides encoding transmembrane regions and/or signal sequences.

Polynucleotides as defined with the present invention also include polynucleotides having variations in the nucleic acid sequence when compared to the identified nucleic acid sequence or having polymorphic sites. With "variants" polynucleotides are meant that differ from the identified nucleic acid sequence but still encode a polypeptide that has a biological, e.g. cytokine, activity similar to the activity of a polypeptide having an amino acid sequence as depicted in SEQ ID NO 1 and/or 2.

Variants may be natural or non-natural variants. Natural variants will include homologues in various avian species. Non-naturally occurring variant may be introduced by mutagenesis. Natural variants may also be allelic variants. An allelic variant is one of several alternate forms of a gene occupying a locus on a chromosome of an organism. Sometimes, a gene is expressed in a certain tissue as a splicing variant, resulting in an altered 5' or 3' mRNA or the inclusion or exclusion of one or more exon sequences. These sequences, as well as the proteins encoded by these sequences, all are expected to perform the same or similar functions and form also part of the invention.

An isolated cDNA sequence may be incomplete due to incomplete transcription from the corresponding mRNA, or clones may be obtained containing fragments of the complete cDNA. Various techniques are known in the art to complete said cDNA sequences, such as RACE (Rapid Amplification of cDNA ends).

Polynucleotides that have a nucleic acid sequence that is a variant of the identified nucleic acid sequence may be isolated by a method comprising the steps of: a) hybridizing a DNA comprising all or part of the identified sequence as reflected in SEQ ID NO 3 or 4, under stringent conditions against nucleic acids being (genomic) DNA or cDNA isolated from avian cells which highly express the polynucleotide of interest; and b) isolating said nucleic acids by methods known to a person skilled in the art.

The hybridization conditions are preferably highly stringent.

According to the present invention the term "stringent" means washing conditions of 1×SSC, 0.1% SDS at a temperature of 65° C.; highly stringent conditions refer to a reduction in SSC towards 0.3×SSC, more preferably to 0.1×SSC. Preferably the first two washings are subsequently carried out twice each during 15-30 minutes. If there is a need to wash under highly stringent conditions an additional wash with 0.1×SSC is performed once during 15 minutes. Hybridization can be performed e.g. overnight in 0.5 M phosphate buffer pH 7.5 with 7% SDS at 65° C. Such hybridization methods are disclosed in any standard textbook on molecular cloning, for example: Molecular Cloning: a laboratory manual, $3^{rd}$ ed.; eds: Sambrook et al., CSHL press, 2001.

As an alternative the isolation method might comprise nucleic acid amplification methodology using primers and/or probes derived from the nucleic acid sequence provided with the present invention. Such primers and/or probes are oligonucleotides that are at least 15 nucleotides in length; preferred oligo's have about 25-50 nucleotides.

Variants or other avian homologues of the sequences depicted in SEQ ID NO 3 and 4 may also be identified by comparing the sequence in silico to other avian sequences that may be comprised in a computer database. Sequences may be compared with sequences in databases using a BLAST program (BLASTF 2.1.2 [Oct. 19, 2000]) (Altschul, S F, T L Madden, A A Schaffer, J Zhang, Z Zhang, W Miller, and D J. Lipman, "Gapped BLAST and PSI-BLAST: a new generation of protein database search programs", Nucleic Acids Res. 1997, 25: 3389-3402).

The bioactivity of proteins according to the invention can be measured in vitro using a proliferation assay, in the following way:

COS-7 cells or chicken cells, e.g. CEF, HD-11, DT40 etc., may be seeded in 35-mm-diameter dishes at $5 \times 10^5$ cells/well. After a culture period of 16 hours cells can be transfected with 1 µg of plasmid DNA encoding chicken IL-12 using Lipofectamin Plus™ (Gibco BRL) according to the manufacturer's instructions. Culture media containing chicken IL-12 can be collected 72 hours after transfection. To check for chicken IL-12 bio-activity a bioassay based on the proliferation of peripheral blood lymphocytes (PBLs) needs to be developed. For this, the cytokine activity, encoded by the transfected plasmid(s), that is released into the culture medium may be analyzed using an adapted protocol of a previously described bioassay (Gately, M. K., Chizzonite, R. & Presky, D. H., "Measurement of human and mouse interleukin-12", in: *Current Protocols in Immunology,* 1997, pp. 6.16.1-6.16.15, edited by J. E. Coligan et al., ed: John Wiley & Sons.)

In this bioassay that was developed specifically for mouse and human IL-12, human PBLs, isolated using Lymphoprep™ (Nycomed), are cultured for 2 days in Iscoves medium containing 5 µg/ml Concanavalin A (ConA). To stimulate formation of blasts recombinant human interleukin-2 is added (50 units/ml) and cells are cultured for 3 additional days. Cells are washed, seeded in 96 well plates ($2 \times 10^4$ cell/well), and cultured in the presence of the culture media of transfected cells. After 48 hours $^3$H-Thymidine (Amersham) is added and the incubation will be continued for 4 hours, whereafter the cells are harvested by an automated cell harvester. The incorporated radioactivity, which is a measure for cell proliferation and therefore IL-12 bio-activity, will be quantified by liquid scintillation counting.

In a further aspect the present invention provides polynucleotides comprising a nucleic acid sequence encoding a polypeptide subunit comprising an amino acid sequence having at least 80% similarity with the amino acid sequence as depicted in SEQ ID NO 1 or 2 respectively. Preferred are polynucleotides encoding polypeptides having at least 95% identity with SEQ ID NO 1 or 2 and more preferred are those polynucleotides encoding polyproteins having at least 97% identity with SEQ ID NO 1 or 2 wherein those encoding polypeptides having at least 98 or 99% are more preferred. Most preferred are polynucleotides encoding the polypeptide of SEQ ID NO 1 or 2. Due to the degeneracy of the genetic code, polynucleotides encoding an identical or substantially identical amino acid sequence may utilize different specific codons. All polynucleotides encoding the polypeptides as defined above are considered to be part of the invention.

In particular preferred polynucleotides according to the invention are isolated polynucleotides having at least 80% identity with the nucleic acid sequence of SEQ ID NO 3 or 4. More preferred are those polynucleotides having at least 90% identity, and yet more preferred at least 95, preferably 99% identity, most preferred 100% identity to the entire sequence of SEQ ID NO 3 or 4.

Such polynucleotides include polynucleotides comprising the nucleic acid sequence depicted in SEQ ID NO 3 and/or 4. A polynucleotide encoding a polypeptide with a sequence as depicted in SEQ ID NO 1 and/or 2 may comprise the nucleic acid sequence as depicted in SEQ ID NO 3 and/or 4.

In a further preferred embodiment of the invention the polynucleotide consists of the nucleic acid sequence as depicted in SEQ ID NO 3 and/or 4.

Examples of polynucleotides showing over 99% homology with the nucleotide sequence depicted in SEQ ID NO 3 are the sequences depicted in SEQ ID NO 6 and 8, which are the coding sequences for the duck and turkey p40 respectively.

The polynucleotides according to the invention may be DNA or RNA, preferably DNA. DNA according to the invention may be obtained from cDNA. Alternatively, the coding sequence might be genomic DNA, or prepared using DNA synthesis techniques. If the polynucleotide is DNA, it may be in single stranded or double stranded form. The single strand might be the coding strand or the non-coding (anti-sense) strand.

Also included within the definition of polynucleotides are modified RNAs or DNAs. Modifications in the bases of the nucleic acid may be made, and bases such as Inosine may be incorporated. Other modifications may involve, for example, modifications of the backbone.

With "isolated" is meant that the polynucleotide is isolated from the natural state, i.e. it has been changed or moved from its natural environment or both. The molecule is separate and discrete from the whole organism with which the molecule is found in nature.

"% Identity" defines the relation between two or more polynucleotides or polypeptides on the basis of a comparison between their aligned sequences.

Identity can be calculated by known methods. Identity, or homology, percentages as mentioned herein are those that can be calculated with the GAP program, running under GCG (Genetics Computer Group Inc., Madison, Wis., USA).

Parameters for polypeptide sequence comparison included the following:

Algorithm: Needleman and Wunsch, J. Mol. Biol. 1970, 48: 443-453.

As a comparison matrix for amino acid alignments the Blosum62 matrix is used (Henikoff and Henikoff, supra) using the following parameters:

Gap penalty: 8

Gap length penalty: 2

No penalty for end gaps.

Parameters for nucleotide comparison that may be used:

Algorithm: Needleman and Wunsch (supra).

Comparison matrix: matches=+10, mismatch=0.

Gap penalty: 50.

Gap length penalty: 3.

The DNA according to the invention will be very useful for in vivo or in vitro expression of the encoded polypeptide in sufficient quantities and in substantially pure form. When the polynucleotides according to the invention are used for expression of the encoded polypeptide, the polynucleotides may include, in addition to the coding sequence for the polypeptide or functional fragment thereof, other coding sequences, for example, leader sequences or fusion portions, such as marker sequences and the like.

Application of p40-based composite cytokines, such as IL-12, IL-23, and $(p40)_2$, may augment micro-organism-induced ongoing immune responses or vaccination-induced immune responses, based on both cellular and humoral immunity. In addition, intervention in the immunological cascade triggered by these cytokines, using e.g. antagonistic doses of (p40)$_2$ may prevent unwanted pathological immune reactions following deregulated overproduction of the p40-based molecules.

The polynucleotides according to the invention may be used in the production of recombinant proteins according to the invention. The polynucleotides may also be used in DNA- or vector vaccines, together with other nucleic acid sequences encoding, for example, immunogenic proteins derived from avian pathogens.

The polynucleotides according to the invention will be very useful for in vivo or in vitro expression of the encoded polypeptide in sufficient quantities and in substantially pure form. When the polynucleotides according to the invention are used for expression of the encoded polypeptide, the polynucleotides may include, in addition to the coding sequence for the polypeptide or functional fragment thereof, other coding sequences, for example, leader sequences or fusion portions, such as marker sequences and the like.

A wide variety of host cell and cloning vehicle combinations may be usefully employed in cloning the nucleic acid sequence according to the invention. A polynucleotide according to the invention may be cloned into an appropriate expression system, such as a bacterial expression system (e.g. *Escherichia coli* DH5α), a viral expression system (e.g. Baculovirus), a yeast system (e.g. *Sacharomyces cerevisiae, Pichia*) or eukaryotic cells (e.g. Cos, BHK, HeLa, HD-11, DT40 or CEF cells). In all systems the polynucleotide is first cloned into an appropriate vector under control of a suitable constitutive or inducible promoter.

In another aspect the present invention therefore relates to a recombinant vector comprising a polynucleotide according to the invention. Suitable vectors are for example cosmids, bacterial or yeast plasmids, wide host range plasmids and vectors derived from combinations of plasmid and phage or virus DNA. Vectors derived from chromosomal DNA are also included. Furthermore an origin of replication and/or a dominant selection marker can be present in the vector according to the invention. The vectors according to the invention are suitable for transforming a host cell. Examples of suitable cloning vectors are plasmid vectors such as pBR322, the various pUC, pEMBL and Bluescript plasmids, or viral vectors such as HVT (Herpes virus of Turkeys), MDV (Marek disease virus), ILT (infectious laryngotracheitis virus), FAV (fowl adenovirus), FPV (Fowlpox virus), or NDV (Newcastle disease virus).

When used in the expression of the polypeptide or functional fragments thereof, a recombinant vector according to the present invention, may further comprise an expression control sequence operably linked to the nucleic acid sequence coding for the protein.

"Operably linked" refers to an arrangement wherein the control sequences are configured so as to perform their usual function, in effecting the expression of the polynucleotide.

Such expression control sequences generally comprise a promoter sequence and sequences which regulate transcription and translation and/or enhance expression levels. Not all of these control sequences need to be present in a recombinant vector as long as the desired polynucleotide is capable of being transcribed and translated. Of course expression control- and other sequences can vary depending on the host cell selected or can be made inducible. Such expression control sequences are well known in the art and extend to any eukaryotic, prokaryotic, or viral promoter or poly-A signal capable of directing gene transcription. Examples of useful promoters are the SV-40 promoter (Science 1983, 222: 524-527), the metallothionein promoter (Nature 1982, 296: 39-42), the heat shock promoter (Voellmy et al., P.N.A.S. USA 1985, 82: 4949-4953), the PRV gX promoter (Mettenleiter and Rauh, J. Virol. Methods 1990, 30: 55-66), the human CMV IE promoter (U.S. Pat. No. 5,168,062), the Rous Sarcoma virus LTR promoter (Gorman et al., P.N.A.S. USA 1982, 79: 6777-6781) or human elongation factor 1 alpha or ubiquitin promoter etc.

After the polynucleotide has been cloned into an appropriate vector, the construct may be transferred into the cell, bacteria, or yeast alone by means of an appropriate method, such as electroporation, CaCl$_2$ transfection or lipofectins. When a baculovirus expression system is used, the transfer vector containing the polynucleotide may be transfected together with a complete baculo genome.

All these techniques are well known in the art and extensively described in protocols provided by manufactures of molecular biological materials (such as Promega, Stratagene, Clontech, and/or Invitrogen) and in literature or reference text books, for instance in Rodriguez, R. L. and D. T. Denhardt, ed., "Vectors: A survey of molecular cloning vectors and their uses", Butterworths, 1988; Current protocols in Molecular Biology, eds.: F. M. Ausubel et al., Wiley N.Y., 1995; Molecular Cloning: a laboratory manual, supra; and DNA Cloning, Vol. 1-4, 2$^{nd}$ edition 1995, eds.: Glover and Hames, Oxford University Press).

The cells transformed with a polynucleotide or a vector according to the invention are likewise part of the present invention. Thus, in another aspect, the present invention provides a cell capable of expressing a recombinant polypeptide, characterized in that the cell comprises a polynucleotide according to the invention encoding the expressed recombinant polypeptide.

The term "recombinant" in this context refers to a polypeptide that is not expressed in the cell in nature. Thus, a host cell which comprises the DNA or expression vector according to the invention is also within the scope of the invention. The engineered host cells can be cultured in conventional nutrient media which can be modified e.g. for appropriate selection, amplification or induction of transcription. The culture conditions such as temperature, pH, nutrients etc. are well known to those ordinarily skilled in the art.

Cells that are transformed with a vector according to the invention may be of prokaryotic or eukaryotic origin, preferably the cells are of eukaryotic origin. Eukaryotic cells according to the invention may be of avian or non-avian origin. Cells that are of non-avian origin may be for example, BHK cells, insect cells, HeLa or COS cells. Preferably the cells are avian cells such as CEF, HD-11 or DT-40 cells.

A transformed cell according to the invention may comprise a polynucleotide according to the invention stably integrated into the genomic material or as part of an autonomously replicating vector.

A cell culture comprising a multitude of cells according to the invention is likewise part of the present invention. Cells according to the invention can be used to express the polypeptide subunits or the complete protein and can be isolated from the cell culture.

The cloning of the nucleotide sequences encoding the p40 and p35 subunits respectively, enables the production of pure proteins, free from other cytokines. This is especially useful in case of the production of antibodies specific for the proteins of the invention. These specific antibodies can be generated via techniques generally available. Preferably the specific antibodies are monoclonal antibodies. Thus the present invention furthermore provides for antibodies specific for the p40 and/or p35 subunits or for the chicken IL-12. The antibodies according to the invention are suitable for use in diagnostics or for isolation and purification of proteins such as avian chicken IL-12 from crude preparations. Moreover, the antibodies can be used to develop assays for quantitative analysis of protein production in vitro or for quantitative measurements of protein levels in vivo.

As already stated above, the proteins and polynucleotides according to the invention are especially useful to enhance the immune response to avian vaccines (i.e. they may be used as or in adjuvants).

Vaccination against an infectious disease aims to elicit an immune response that limits clinical symptoms associated with infection by a pathogen. It is important that the correct type of immune reaction is triggered, since many types of immune mechanisms that can be activated are inadequate for control of the particular pathogen. Low responsiveness to vaccine antigens can be overcome by administering the antigens in combination with adjuvants. Adjuvants are defined as those components of a vaccine formulation other than the antigen which contribute to enhanced immune responsiveness to the antigen, e.g. aluminum salts, oil emulsions, derivatives of muramyl peptide, monophosphoryl lipid A, liposomes, QS21™, MF-59™, Iscoms™, and the like.

The cellular and molecular mechanisms that are activated following vaccination are strongly influenced by the choice of adjuvant that is administered together with the vaccine antigen. Hence the selection of adjuvants may be as critical as the choice of vaccine antigens themselves in providing optimal efficacy.

Proteins according to the invention, in particular the chicken IL-12, may have a potent adjuvant effect on the immune response of a subject to a vaccine. Thus in another embodiment the invention provides for an adjuvant composition comprising an effective adjuvant amount of a protein according to the invention, in particular chicken IL-12. The adjuvant composition can be administered concomitantly or sequentially with a vaccine formulation.

The protein(s) according to the invention can be included in the vaccine formulation. Thus in another embodiment the present invention provides for a vaccine comprising at least one active agent, an effective adjuvant amount of a protein according to the invention, preferably chicken IL-12, and a pharmaceutically acceptable carrier or diluent.

A protein according to the present invention can be a molecule comprising the whole of the p40 and/or p35 sub-unit(s) or fragments thereof, provided said fragments have retained their ability to act as a cytokine (for example, when used in a vaccine, to retain their adjuvanting ability).

An adjuvant composition according to the present invention comprises a protein according to the invention, preferably chicken IL-12, and a pharmaceutically acceptable carrier. Suitable pharmaceutical carriers are water, saline, and the like. Additionally, the adjuvant composition may comprises one or more other adjuvants such as oil emulsions, aluminum salts, derivatives of muramyl dipeptide, monophosphoryl lipid A, liposomes, QS21 ™, MF-59™, Iscoms™, and the like. The proteins according to the invention may also be used in conjunction with other cytokines.

The adjuvant composition according to the invention may, in the alternative, comprise a DNA plasmid capable of expressing a protein according to the invention. Said DNA plasmid comprises DNA sequences encoding a protein according to the invention, preferably chicken IL-12, operably linked to transcriptional regulatory sequences. Nucleotide sequences encoding for other cytokines that are used in conjunction with a protein according to the invention can be present on the same DNA plasmid or on a separate plasmid. Upon administration of such a DNA adjuvant composition to a subject, host cells take up and express encoded genes on the inoculated DNA, resulting in in vivo expression of the proteins according to the invention, for example, chicken IL-12.

A vaccine according to the invention comprises at least one active agent and an effective adjuvant amount of a protein according to the invention, i.e. in an amount which will cause the vaccinated subject to produce an enhanced immunological response as compared to the vaccine without said protein.

The required effective amount in an adjuvant composition or vaccine according to the invention is dependent on the type of active agent used, the type of pathogen immunized against, as well as the type of vaccinated subject. Determination of the effective amount is well within the routine skills of the practitioner, and will generally be in the amount of 0.001 to 500 µg/dose. Preferably the amount will be between 0.01 and 50 µg/dose, more preferably 0.1 to 5 µg/dose.

The active agent for use in a vaccine according to the invention can be of viral, bacterial or parasitic origin. The active agent may either be the whole pathogen which causes the disease, or may consist of components derived from said pathogen. In the event the active agent is a whole pathogen, said pathogen may be a live pathogen or an inactivated pathogen. Live pathogens are considered to be either attenuated or naturally occurring mild strains of said pathogen. Inactivated pathogens are pathogens killed by chemical or physical means, that is, the inactivated or "killed" pathogen is no longer capable of replication. Suitable means for chemical inactivation are formaldehyde, glutaraldehyde, β-propiolactone, ethyleneimine and derivatives, and the like. Suitable means for physical inactivation are UV radiation, γ-radiation, "heat-shock", X-radiation, and the like. Alternatively, the active agent may constitute one or more components derived from said disease causing pathogen, e.g. purified protein, protein-polysaccharide, protein-lipopolysaccharides, lipopolysaccharides, and the like.

The active agent may be a DNA plasmid capable of in vivo expression of a pathogen or selected components derived from said pathogen. In addition, the vaccine may comprise a DNA plasmid capable of expressing a protein according to the invention in vivo. The DNA encoding said protein adjuvant and the DNA encoding said pathogen or selected components may be present on one and the same plasmid, or may be present on separate plasmids. Upon administration of the DNA vaccine to a subject, host cells will take up and express in vivo said active agent as well as said protein according to the invention. DNA vaccines are for example described in U.S. Pat. No. 5,580,859.

Pharmaceutically acceptable carriers or diluents that can be used to formulate an adjuvant composition or a vaccine composition according to the invention are sterile and physiologically compatible such as for example an aqueous buffer, a saline solution and the like. In addition stabilizers, preservatives and the like may be added to these compositions.

The compositions of the present invention may take any form that is suitable for oral or parenteral administration. For oral use, the adjuvant or vaccine compositions according to the invention may be formulated as solutions, syrups, suspensions, tablets, capsules and the like. For parenteral use, the compositions according to the present invention may be formulated in a form suitable for injection such as suspensions, solutions, dispersions, emulsions, and the like. Preparation of the compositions according to the present invention is carried out by means conventional for the skilled person.

Preferred administration routes are parenteral routes, e.g. intramuscular injection, intravenous injection, intradermal injection, subcutaneous injection, and mucosal routes, e.g. nasal drops, eye drops, (aerosol) sprays, and the like.

The following examples will illustrate the invention without limiting the invention thereto.

BRIEF DESCRIPTION OF THE FIGURES

FIG. 1: DNA and protein sequence of clone pat.pk0055.c11 (=chicken ChIL-12 p35) (SEQ ID NO 4 and 2, respectively).

FIG. 2: Sequence of clone chicken ChEST582p2; 5' and 3' primers (SEQ ID NO 18 and 17, respectively)

FIG. 3: DNA and protein sequence of clone pND89 (=chicken ChIL-12 p40) (SEQ ID NO 3 and 1, respectively).

FIG. 4: DNA and protein sequence of clone pND115 (=Duck IL-12 p40) (SEQ ID NO 6 and 5, respectively).

FIG. 5: DNA and protein sequence of clone pND117 (Turkey IL-12 p40) (SEQ ID NO 8 and 7, respectively).

FIG. 6: DNA homology of chicken p40 to p40 sequences of duck and turkey. (SEQ ID NO 3, 6 and 8, respectively FIG. 7: Protein homology of chicken p40 to p40 sequences of duck and turkey. (SEQ ID No 1, 5 and 7, respectively).

EXAMPLES

Materials and Methods for All Examples

Figure 8:
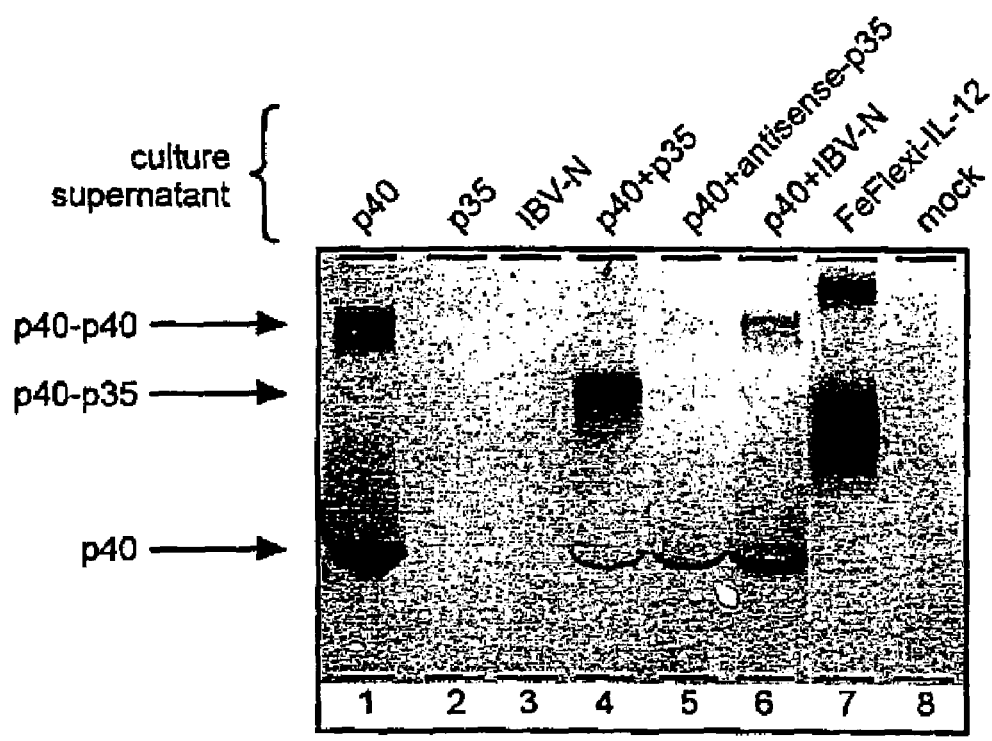
FIG. 8: Western blot analysis of COS-7 cell culture supernatants after transfection with chicken IL-12 and other cDNA molecules (mock=empty vector control).

Cell Culture and LPS Treatment.

The chicken cell lines HD-11 (macrophage origin) and DT-40 (B-cell origin) were grown as cell suspensions in RPMI (supplemented with 10% fetal calf serum, 100 µg/ml streptomycin, 100 units/ml penicillin, 2 mM glutamin and 1 mM pyruvate) and DMEM (supplemented with 8% fetal calf serum, 2% chicken serum, 2 mM glutamin, 100 µg/ml streptomycin, 100 units/ml penicillin and 1 mM pyruvate), respectively. Lipopolysaccharide (LPS) treatment included the incubation of cells with 5 µg/ml LPS for 5 h. After the treatment, cells were washed 2-times with phosphate buffered saline and subsequently used for RNA isolation or stored at −70° C. Cells were maintained in a humidified atmosphere of 5% $CO_2$ at 37° C.

The mammalian cell line COS-7 (African green monkey kidney cells) was grown in DMEM (supplemented with 10% FCS, 2 mM glutamine, 100 µg/ml streptomycin, 100 U/ml penicillin and 1 mM pyruvate)

Chicken, Duck and Turkey Organs and LPS Treatment.

Three weeks old Normal White Leghorn specific pathogen free (SPF) chickens were derived from the Intervet animal facilities and housed under SPF conditions. The animals received water and food ad libitum.

Freshly isolated chicken, duck or turkey organs, i.e. spleen and kidney, were mashed using a sieve and Hanks buffer. Cells were pelleted at 1500 rpm for 3 minutes at room temperature and washed 2-times using the same procedure. Duck and turkey cells were subsequently used for RNA isolation. Chicken cells were resuspended in RPMI supplemented with 10% chicken serum, 100 µg/ml streptomycin and 100 units/ml penicillin, and grown for 16 h. Some cells were incubated with 5 µg/ml LPS for 5 h. After the treatment, cells were washed 2-times with phosphate buffered saline and subsequently used for RNA isolation or stored at −70° C. Cells were maintained in a humidified atmosphere of 5% $CO_2$ at 41° C.

RNA Isolation.

Total RNA was isolated using Trizol Reagent™ (Gibco-Invitrogen) as described by the manufacturer. RNA quality was checked on a 1% agarose gel.

RT-PCR, PCR and Sequence Reactions.

Two µg of total RNA were reverse-transcribed into cDNA using the Superscript II RT™ protocol (Gibco-Invitrogen). This newly made cDNA was subsequently used as template for PCR amplification. For this, 1 µl of RT-cDNA reaction (10-20 ng of plasmid cDNA template) was mixed with 0.5 µl of 1 unit/µl Supertaq™ (HT Biotechnology Ltd.), 1 µl of 10 ng/µl of each primer, 1.6 µl of 2 mM dNTPs, and 2 µl of 10×ST PCR buffer (HT Biotechnology Ltd.) in a final volume of 20 µl. The reaction cycling conditions were 94° C. for 2 min, then 30 cycles of 94° C. for 30 s, 55° C. for 1 min, 72° C. for 1 min 30 s, then 72° C. for 2 min for a final extension. The PCR products were gel-purified using the Qiaquick Gel Extraction Kit™ (Qiagen), cloned into the pDrive™ vector (Qiagen PCR Cloning kit, Qiagen) or into the pCR2.1-TOP™ vector (TA Cloning kit, Invitrogen).

Plasmid DNA was purified using the Qiagen Plasmid Midi Kit™ (Qiagen). For general PCR-reactions, in which 10 ng of a plasmid template is being used, the same cycling conditions are used as described above.

All clones were extensively sequenced in both 5' and 3' directions using a DNA sequencing kit (BigDye Terminator v3.0 Cycle Sequencing Ready Reaction™, Applied Biosystems). Sequences were analyzed with the Sequencher™ 4.0 software (Gene Codes Corporation).

Sequence Analysis.

Sequence analysis, included use of Blast searches (through an internal server, InterBLAST, from Intervet Innovation, Schwabenheim, Germany), the Wisconsin Package™ Version 10.2 (Genetics Computer Group; GCG), Sequencher™ 4.0 (Gene Codes Corporation), OMIGA™ 2.0 (Oxford Molecular Ltd.) and of GeneDoc™ 2.6.

Chicken (Ch) IL-12 p35, ChIL-12 p40, ChFlexi-IL-12 and Feline (Fe) Flexi-IL-12 Eukaryotic Expression Constructs ChIL-12 p35. Full length ChIL-12 p35 (clone pat.pk0055.c11), originally cloned in pcDNA3™ (Invitrogen) (Tirunagaru, V G et al., Genomics 2000, 66:144), was excised from pcDNA3 using EcoRI and NotI and cloned into the corresponding restriction sites of the eukaryotic expression vector pcDNA3.1(+)™ (Invitrogen). The EcoRI/NotI ChIL-12 p35 fragment was also cloned into the corresponding restriction sites of pcDNA3.1(−)™ (Invitrogen) to obtain an anti-sense control construct.

ChIL-12 p40. Full length ChIL-12 p40, present in a cDNA library constructed from pooled T and B cells isolated from vaccinated chickens and recloned into pDrive™ (Qiagen), was excised from pDrive using NotI and HindIII and cloned into the corresponding restriction sites of the eukaryotic expression vector pcDNA3.1(−) (Invitrogen).

ChFlexi-IL-12. A single chain chicken IL-12 molecule was generated by a strategy described by McMonagle et al. (Equine Vet. J. 2001, 33: 693).

The following primers were used to amplify ChIL-12 p35 without the putative 35 amino acid signal peptide sequence (as determined by the SPScan program from the Wisconsin Package (supra) and that introduced a 5'-BamHI and a 3'-HindIII restriction site:

5'-TTGGATCCGGTGGCGGCGGATCTCTGC-CACCTCCTGCCCA-3' (SEQ ID NO 9), and

5'-CCAAGCTTTTACATCTCTGCAGT-GAGGGCACTCAGGTAGC-3' (SEQ ID NO 10).

For ChIL-12 p40 the following primers were used that introduced a 5'-NotI and a 3'-BamHI restriction site:

5'-TTGCGGCCGCCATGTCTCACCTGC-TATTTGCCTTACTTTC-3' (SEQ ID NO 11) and

5'-TGGATCCACCACCGCCCGAGCCACCGC-CACCTCTGCAAAGCGTGG-3' (SEQ ID NO 12).

Both PCR fragments were separately cloned into pCR2.1-TOPO™ (Invitrogen) and extensively sequenced. ChIL-12 p40 was excised from pCR2.1-TOPO as a NotI/BamHI fragment and cloned into the corresponding restriction sites of the pcDNA3.1(−) vector (Invitrogen). The ChIL-12 p35 was excised from pCR2.1-TOPO as a BamHI/HindIII fragment and cloned into the corresponding restriction sites of the [ChIL-12 p40]-[pcDNA3.1(−)] construct downstream of the p40 fragment. This resulted in a single chain p40-p35 heterodimeric construct in which the p40 chain is linked to the p35 chain by an in-frame $(Gly_4Ser)_3$-linker; this molecule was designated ChFlexi-IL-12. FeFlexi-IL-12. Feline IL-12 was cloned into the eukaryotic pCI-neo™ vector (Promega) (Dr. L. Nicolson, Univ. of Glasgow Veterinary School, UK) producing a construct similar to the ChFlexi-IL-12.

Transient Expression of cDNA Clones in COS-7 Cells

COS-7 cells were transfected with 1.5 µg of each cDNA construct using the Invitrogen Life Technologies Lipofectamine™ reagent (as described by the manufacturer) and cultured in 3-cm dishes with DMEM (without FCS and penicillin/streptomycin). After 8 h, transfected cells were washed and cultured in DMEM with penicillin/streptomycin and 10% FCS. After 72 h incubation at 37° C./5% $CO_2$ the cell culture supernatants were harvested and centrifuged at 13,000 rpm for 10 min at 4° C. to remove cell debris. The supernatants were analyzed via Western blotting and used immediately or stored at −70° C.

Western Blot Analysis

Cell culture supernatants from transfected COS-7 cells were size fractionated using 4-12% Nu-PAGE T (Invitrogen) and blotted onto nitrocellulose filters (Schleicher & Schuell). Western blots were blocked in 3% skimmed milk (MPBS) in PBS, and subsequently incubated with a polyclonal antibody that was raised against a FeIL-12 p40 peptide diluted 1:300 in MPBS. Blocking and antibody incubation were each performed for 1 h at room temperature. After extensive washing (3 times 5 min), blots were incubated with alkaline peroxidase (AP)-conjugated goat anti-rabbit IgG antibodies (Sanbio) diluted 1:1000 in MPBS for 1 h at room temperature. After washing (3 times 5 min), bound AP-labeled secondary antibodies were visualized via staining.

Bioactivity Assays for Chicken (Ch) IL-12

NO-assay for the induction of splenic ChIFN-γ by ChIL-12. Chicken spleen cells were freshly isolated and seeded in triplicate in a 96-well plate at a density of $0.5 \times 10^6$ cells/well in 100 µl and incubated with 50 µl of serial dilutions of cell culture supernatants from COS-7 cells transfected with cDNA clones encoding ChIL-12 p40, ChIL-12 p40 mixed with ChIL-12 p35, ChFlexi-IL-12, FeFlexi-IL-12 or with an empty pcDNA3.1 plasmid (mock). Forty-eight hours after the addition of proteins, supernatants (75 µl) were collected and analyzed for the presence of biologically active ChIFN-γ. For this, 100 µl of $1.5 \times 10^6$/ml HD-11 cells were incubated with 75 µl of the collected supernatants for 24 h at 37° C./5% $CO_2$ in 96-well plates. Activation of HD-11 cells by ChIFN-γ was measured as a function of nitrite accumulation in the culture supernatants using the Griess assay (Ding, A H et al., J. Immunol. 1988, 141: 2407; Stuehr, DJ, and CF Nathan, J. Exp. Med. 1989, 169:1543).

Assay for spleen cell proliferation by ChIL-12. After removing 75 µl of the supernatants (see NO-assay for the induction of splenic ChIFN-γ by ChIL-12 section) 50 µl medium and 18.5 kBq methyl-$^3$H-Thymidine (25 µl per well) were added to the remaining 75 µl in the 96-well plate and incubated for 18-20 h at 41° C./5% $CO_2$. After incubation the incorporated radioactivity was counted using an LKB Betaplate™ β-counter.

Statistical Analysis

The significance of the differences between the means of NO-production or between the means of cell proliferation was analyzed using the Student's t-test. Differences were considered significant at a confidence level of 95% ($P<0.05$).

Example 1

Isolation and Sequence Analysis of Clone pat.pk0055.c11 Encoding the Chicken IL-12 p35 Subunit (ChIL-12 p35)

Analysis of the open reading frame (nucleotides 1-618) of cDNA clone pat.pk0055.c11 (see FIG. 1), which was isolated from a high throughput sequencing project of the chicken Con A stimulated T cell cDNA library (Tirunagaru et al., supra) showed that it is homologous to the IL-12 p35 cDNA sequences of human (43% overall homology, M65271 in EMBL/Genbank), sheep (45% overall homology, AF173557 in EMBL/Genbank), horse (48% overall homology, Y11130 in EMBL/Genbank), cat (43% overall homology, Y07761 in EMBL/Genbank), bovine (45% overall homology, U14416 in EMBL/Genbank), mouse (42% overall homology; M86672 in EMBL/Genbank) and woodchuck (45% overall homology, X970189 in EMBL/Genbank) A multiple alignment of the Ch IL-12 p35 protein encoded by pat.pk0055.c11 to human, sheep, horse, cat, bovine, mouse and woodchuck IL-12 p35 proteins yields an overall amino acid homology of 27%, 25%, 30%, 24%, 25%, 29% and 21%, respectively. When removing the first 64 aa (residues 1-64) of pat.pk0055.c11 the homologies to human, sheep, horse, cat, bovine, mouse and woodchuck IL-12 p35 proteins increases to 33%, 32%, 37%, 25%, 32%, 34% and 28%, respectively, indicating that the N-terminal fragment of pat.pk0055.c11 is not as highly conserved as the rest of the protein. Based on these sequence homologies we conclude that clone pat.pk0055.c11 encodes the chicken IL-12 p35 subunit.

Example 2

Isolation of Clone pND89 Encoding the Chicken IL-12 p40 Subunit (ChIL-12 p40)

The coding sequence, i.e. nucleotides 35-1042, of the mouse Interleukin 12 p40 subunit (MuIL-12 p40; EMBL/Genbank Accession number M86671) was used to search the UMIST/Nottingham/Dundee Chicken EST Repository Database using the tBlastX program. A chicken EST sequence (clone ID: ChEST582p2; EST name 603603708F1; derived from adult kidney) was retrieved that showed 51% identity with aa 251-279 and 66% identity with aa 310-327 of the MuIL-12 p40 sequence. No Genbank Accession number has been assigned to this ChEST582p2 clone and no annotations pointing in the direction of IL-12 were made by the owners of this Chicken EST database. A database search in the same chicken EST database with this ChEST582p2 clone did not result in a longer or full length clone. A similar database search in the U.D. Chick EST database with the coding sequence, i.e. nucleotides 35-1042, of MuIL-12 p40 (EMBL/Genbank Accession number M86671) did not result in a valid hit using the BlastN program nor did a search with the ChEST582p2 clone result in a longer or full length clone.

The identified ChEST582p2 clone is 848 nucleotides long of which nucleotides 3-233 (which includes a stopcodon) encode a 76 aa long polypeptide (see FIG. 2). A multiple alignment of the predicted ChEST582p2 protein sequence showed that it aligns to the most C-terminal part of MuIL-12 p40 (35% overall homology; M86671 in EMBL/Genbank), and to the C-terminal part of IL-12 p40 of several other species including human (43% overall homology, M65272 in EMBL/Genbank), sheep (43% overall homology, AF004024 in EMBL/Genbank), horse (43% overall homology, Y11129 in EMBL/Genbank), cat (43% overall homology, Y07762 in EMBL/Genbank), bovine (42% overall homology, U11815 in EMBL/Genbank) and woodchuck (51% overall homology, X97019 in EMBL/Genbank).

To clone the full length chicken IL-12 p40 protein subunit (ChIL-12 p40), three approaches have been used.

In the first approach 3 degenerated primers:

5'-ATGTGTCACCAGYRGTTGGTCMTCTCYTG-3' (SEQ ID NO 13),

5'-ATGTGTCYTCAGMAGYTRRYCATCTCCTG-3' (SEQ ID NO 14), and

5'-ATGTGTCWYCAGYRGTTGGTCMTCTCCTG-3') (SEQ ID NO 15), and 1 specific 5'-end primer

5'-ATGCACCCTCAGCAGTTGGTCGTTTCCTG-3' (SEQ ID NO 16), based on the 5'-end of human (M65272 in EMBL/Genbank), reddeer (US7752 in EMBL/Genbank), horse (Y11129 in EMBL/Genbank), sheep (AF004024 in EMBL/Genbank), mouse (M86671 in EMBL/Genbank) and woodchuck (X97019 in EMBL/Genbank) were designed. In combination with a 3'-ChESTp582p2 primer

5'-TTATCTGCAAAGCGTGGACCACTCACTC-CAGGAT-3' (SEQ ID NO 17)

(complementary to nucleotide positions 233-200 in FIG. 2) an RT-PCR reaction was performed on total RNA isolated from chicken HD-11 (macrophage) cells, chicken DT-40 (B) cells, chicken kidney cells and chicken spleen cells treated with or without 5 µg/ml lipopolysaccharide (LPS). Surprisingly, none of the primer combinations resulted in a PCR-product. As a control, an RT-PCR reaction was performed simultaneously using a 5'-end ChESTp582p2 primer.

5'-ACCTGGACATATCCCAAGACCTGGAGCACA-3' (SEQ ID NO 18)

(nucleotide positions 12-41 in FIG. 2) and the 3'-end ChESTp582p2 primer (SEQ ID NO 17, supra). This primer combination resulted in a PCR-fragment of 200 nucleotides. These results indicate that it is not possible to obtain a full length chicken IL-12 p40 molecule by using an RT-PCR approach based on 5'-end IL-12 p40 sequences from human, reddeer, horse, mouse or woodchuck with degenerated primers in combination with a specific 3'-end primer.

In the second approach we used plasmid pools isolated from a HD-11 cDNA library that was constructed from chicken HD-11 (macrophage) cells stimulated for 5 h with 5 µg/ml of LPS (Sick C, Schneider K, Staeheli P, Weining K C. Novel chicken CXC and CC chemokines. Cytokine 2000, 12:181-186) In this library cDNA molecules are unidirectionally cloned between the EcoRI and XhoI sites of the eukaryotic expression vector pcDNA1. In a PCR-reaction with a 5'-end pcDNA1 vector primer 116 nt upstream of the EcoRI restriction site

5'-CTGGCTAACTAGAGAACCCACTGCT-TACTGGCTT-3' (SEQ ID NO 19)

(nucleotide positions 2918-2951 of vector pcDNA1) and the 3'ChEST582p2 primer (SEQ ID NO 17, supra) a PCR-fragment of ~1000 nucleotides was obtained that was cloned into pDrive™ (Qiagen).

In the third approach we used plasmid pools isolated from a cDNA library that was constructed from pooled T and B cells isolated from vaccinated chickens. In this library cDNA molecules are unidirectionally cloned between the NotI and EcoRI sites of the eukaryotic expression vector pBlueScript™ (Stratagene). In a PCR-reaction with a 5'-end pBlueScript vector primer approximately 120 nucleotides upstream of the NotI restriction site and the 3' ChEST582p2 primer (SEQ ID NO 17, supra) a PCR-fragment of ~1000 nucleotides was obtained that was cloned into pDrive.

To investigate whether this clone, designated pND89, contains the ~200 nt IL-12 p40 fragment at the 3'-end, a PCR reaction using pND89 as template in combination with the 5'ChESTp582p2 (SEQ ID NO 18, supra) and the 3' ChESTp582p2 primer (SEQ ID NO 17, supra) was performed. The results showed a PCR-fragment of ~200 nucleotides indicating that the ~1000 nt long pND89 cDNA clone contains the 222 nt long IL-12 p40 fragment.

Example 3

Sequence Analysis of cDNA Clone pND89

Clone pND89 was extensively sequenced which revealed that the cDNA clone (from start to stop) is 948 nucleotides long and encodes a protein of 315 aa (see FIG. 3. Analysis of the pND89 cDNA sequence containing the open reading frame (nucleotides 1-948) showed that it is homologous to the IL-12 p40 cDNA sequences of human (57% overall homology, M65272 in EMBL/Genbank), sheep (56% overall homology, AF004024 in EMBL/Genbank), horse (57% overall homology, Y11129 in EMBL/Genbank), cat (55% overall homology, Y07762 in EMBL/Genbank), bovine (56% overall homology, U11815 in EMBL/Genbank), mouse (55% overall homology; M86671 in EMBL/Genbank) and woodchuck (57% overall homology, X97019 in EMBL/Genbank). A multiple alignment of the Ch IL-12 p40 protein encoded by pND89 to human, sheep, horse, cat, bovine, mouse and woodchuck IL-12 p40 proteins yields an amino acid homology of 41%, 40%, 40%, 42%, 39%, 36% and 41%, respectively. Sequence analysis further revealed the presence of a signalpeptide with the cleavage site between aa 20-21 resulting in a signal peptide of 20 aa and a mature protein of 295 aa. The presence of a WSXWS box (aa 305-311), an Ig-like C2-type domain (aa residues 41-94) and a fibronectin type-III domain (aa residues 228-308), which are both characteristic for IL-12 p40, were confirmed by similarity. These sequence homologies prove that clone pND89 encodes the chicken IL-12 p40 subunit.

Example 4

Isolation and Sequence Analysis of Clones pND115 and pND117 Encoding the Duck and Turkey IL-12 p40 Subunits, Respectively Using the chicken IL-12 p40 sequence and the existing high homology between chicken and duck/turkey, we tried to clone the duck and turkey IL-12 p40 subunits. In combination with a 5'-end chicken IL-12 p40 primer

5'-ATGTCTCACCTGCTATTTGC-3' (SEQ ID NO 20)

(nucleotide positions 1-20 in FIG. 3) and a 3'-end chicken IL-12 p40 primer

Figure 6:
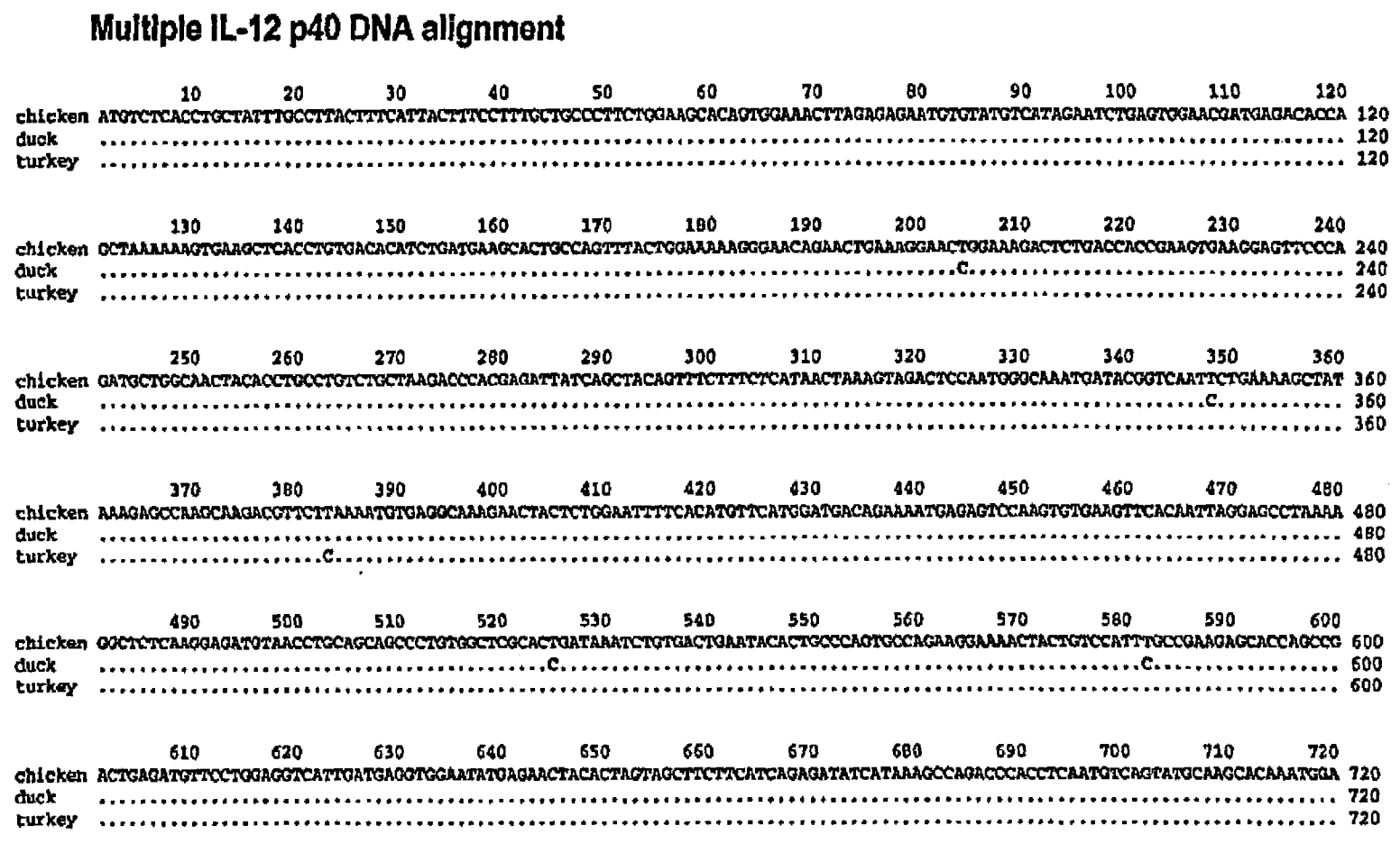

5'-TTATCTGCAAAGCGTGGACCACT-3' (SEQ ID NO 21)(complementary to nucleotide positions 948-926 in FIG. 3) an RT-PCR reaction was performed on total RNA isolated from either duck or turkey spleen and kidney cells. From the RT-PCR reactions PCR fragments of ~000 nt were obtained that were subsequently cloned into the pCR2.1™ vector (Invitrogen). The duck clone was designated pND115 and the turkey clone pND117. Clones pND115 and pND117 were extensively sequenced which revealed that both cDNA clones (from start to stop) are 948 nucleotides long and encode proteins of 315 aa (see FIGS. 4 and 5). Analysis of the pND115 and pND117 cDNA sequences containing the open reading frame (nucleotides 1-948) showed that both are >99% identical to the IL-12 p40 cDNA sequence of chicken (see FIG. 6). A multiple alignment of the predicted pND115 and pND117 proteins showed that pND115 is identical to chicken IL-12 p40 and that pND117 is >99% identical to the chicken IL-12 p40 protein (see FIG. 7). The small differences in homology between pND115, pND117 and chicken IL-12 p40 are the result of small substitutions in the cDNA sequence which results in silent amino acid residue mutations for both pND115 and pND117, and in 1 amino acid residue change for pND117 (see FIG. 7). Based on these high sequence homologies we conclude that clone pND115 encodes the duck IL-12 p40 subunit and that clone pND117 encodes the turkey IL-12 p40 subunit.

Example 5

Characterization of Recombinant Chicken (Ch) IL-12

To detect secreted ChIL-12 p40 and ChIL-12 p35 subunits after (co-) transfection of COS-7 cells non-denaturing Western blot analysis was applied. For this, a polyclonal antibody which was raised against a peptide of the Feline (Fe) IL-12 p40 subunit was used. With this anti-FeIL-12 p40-peptide antibody, ChIL-12 p40 and the ChIL-12 p40 homodimer: ChIL-12 p80 (Ch (p40)$_2$) could be detected in the supernatants of transfected COS-7 cells (FIG. 8, lane 1). In the supernatants from COS-7 cells transfected with both ChIL-12 p35 and ChIL-12 p40 the heterodimeric ChIL-12 p70 protein (ChIL-12) (FIG. 8, lane 4) could be detected indicating that the p40 and p35 chain interact with each other into the heterodimeric IL-12 p70 molecule. The formation of ChIL-12 p70 was more efficient than the formation of homodimeric ChIL-12 p80 as no or only very small amounts of ChIL-12 p80 could be detected. Also, formation of ChIL-12 p70 is specific as co-transfection of ChIL-12 p40 cDNA with anti-sense ChIL-12 p35 cDNA or with a cDNA construct encoding an irrelevant viral protein (IBV-N) did not result in heterodimerization (FIG. 8, lanes 5-6).

Example 6

Bioactivity of Chicken IL-12

[1] ChIL-12 Dependent Induction of ChIFN-γ

Figure 9:
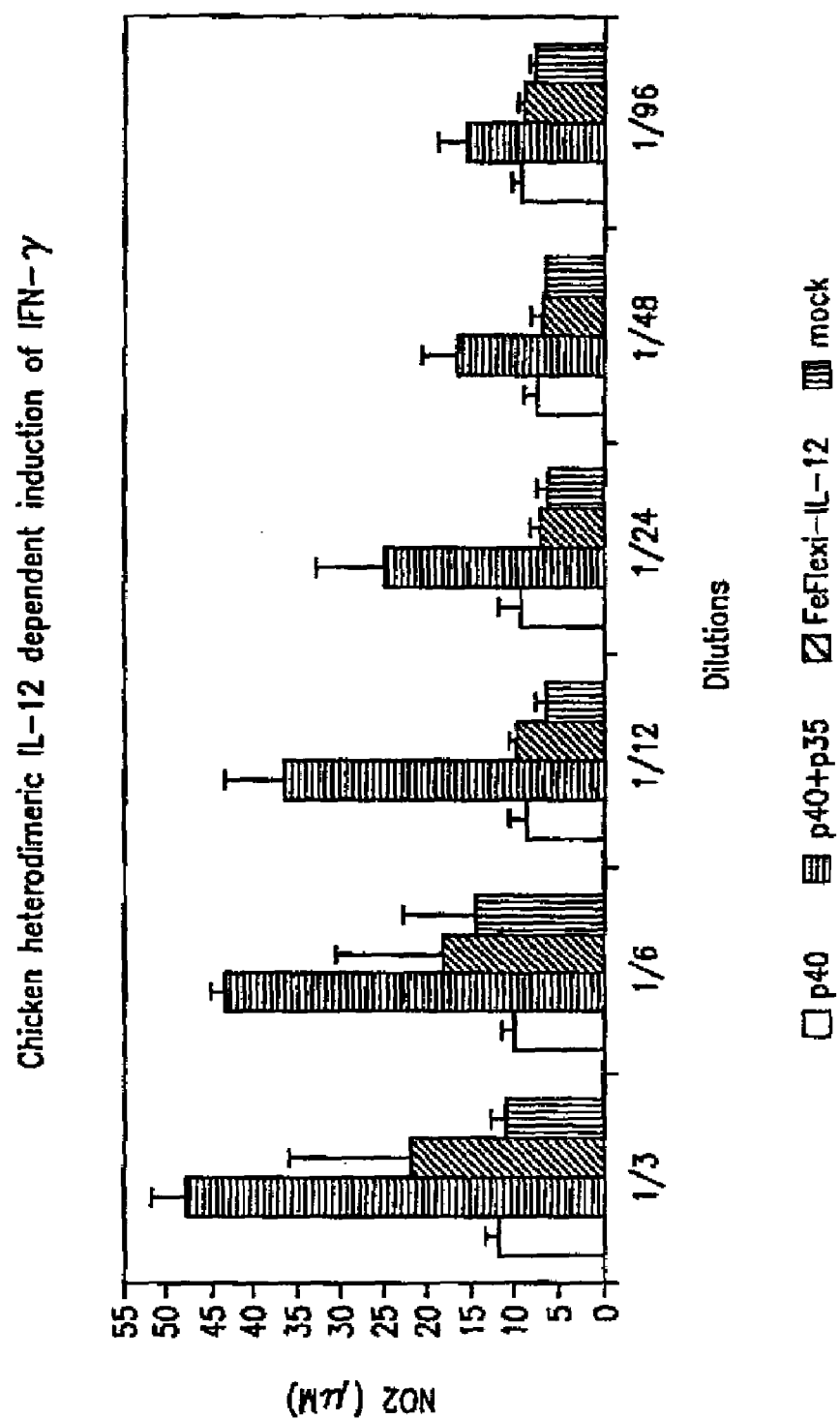
FIG. 9: Chicken heterodimeric IL-12 dependent induction of IFN-γ (Fe=feline; mock=empty vector control).

A hallmark of IL-12 activity in mammals is its induction of IFN-γ by T lymphocytes. Therefore, the IFN-γ levels were assessed in the culture medium of freshly isolated chicken spleen cells incubated with dilutions of various proteins isolated after transient (co-)expression in COS-7 cells. ChIFN-γ was measured as a function of nitrite accumulation using HD-11 cells and the Griess assay. As shown in FIG. 9, only heterodimeric ChIL-12 p70 (a co-transfection of ChIL-12 p40 with ChIL-12 p35) is able to induce production of IFN-γ in chicken spleen cells in a concentration dependent manner. Transfection of mock vector or of ChIL-12 p40 alone, could not induce ChIFN-γ secretion to a level anywhere comparable to the heterodimeric ChIL-12 p70. Next to this it is clear that only species specific IL-12 induces IFN-γ in chicken spleen cells as the FeFlexi-IL-12, induced no significant amounts of ChIFN-γ. The differences in NO-production between ChIL-12 p40 and ChIL-12 p70 (a co-transfection of ChIL-12 p40 with ChIL-12 p35), and between ChIL-12 p70 and FeFlexi-IL-12 were significant ($P<0.05$). Taken together, these results indicate that ChIL-12 is bioactive and that the induction of IFN-γ via chicken spleen cells is ChIL-12 dependent.

Example 7

Bioactivity of Chicken IL-12

[2] ChIL-12-Dependent Proliferation of Chicken Spleen Cells

Figure 10:
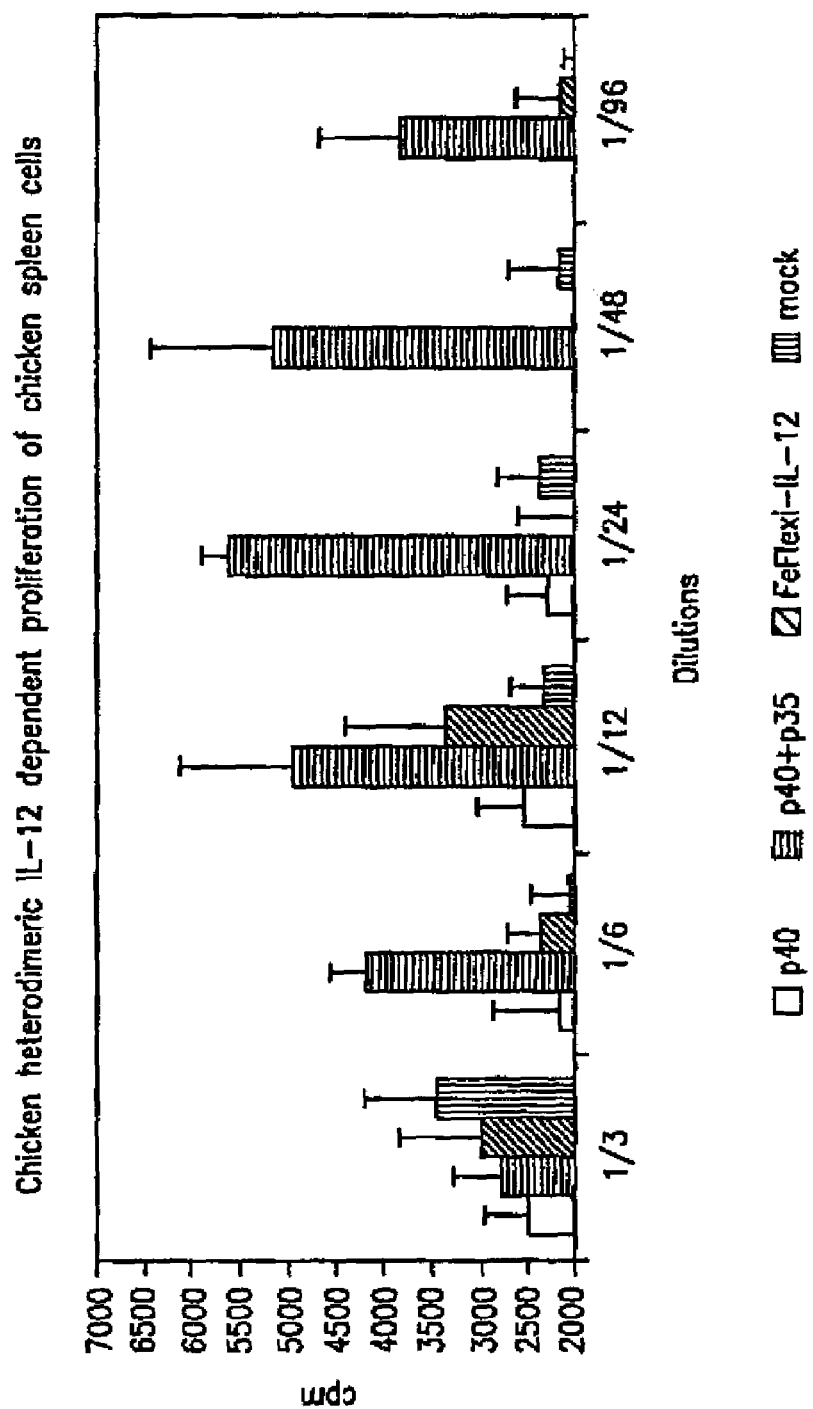
FIG. 10: Chicken heterodimeric IL-12 dependent proliferation of chicken spleen cells (Fe=feline; mock=empty vector control).

Another characteristic of IL-12, shared with several other cytokines, is its induction of T cell proliferation. The growth response of freshly isolated chicken splenocytes to various proteins, isolated after transient (co-) expression in COS-7 cells, was measured by a cell proliferation assay. Only heterodimeric ChIL-12 p70 (a co-transfection of ChIL-12 p40 with ChIL-12 p35) was able to induce the proliferation of chicken spleen cells (FIG. 10). The relatively low proliferation data observed for the first dilutions are possibly explained by overdose effects for this parameter. Neither ChIL-12 p40 alone nor FeFlexi-IL-12 were able to induce similar proliferative responses. From ⅙ dilution on the differences in proliferation between ChIL-12 p40 and ChIL-12 p70 (a co-transfection of ChIL-12 p40 with ChIL-12 p35), and between ChIL-12 p70 and FeFlexi-IL-12 were significant (P<0.05). Taken together, these results prove that ChIL-12 is bioactive and that the molecule is able to induce proliferation of chicken spleen cells.

Example 8

Bioactivity of Chicken IL-12

[3] Bioactivity of Single Chain ChFlexi-IL-12

Figure 11:
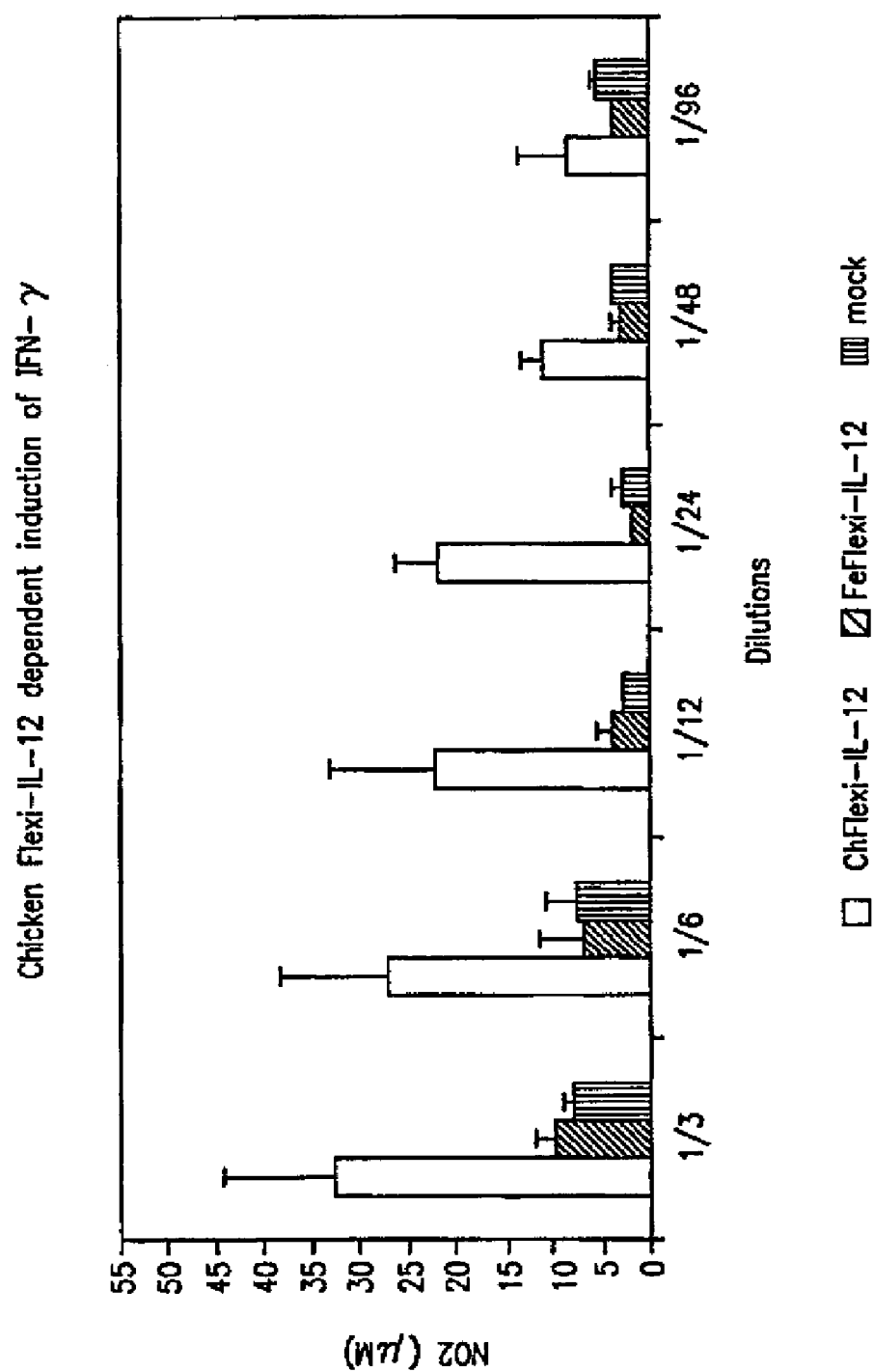
FIG. 11: Chicken Flexi-IL-12 dependent induction of IFN-γ (Fe=feline; mock=empty vector control).
Figure 12:
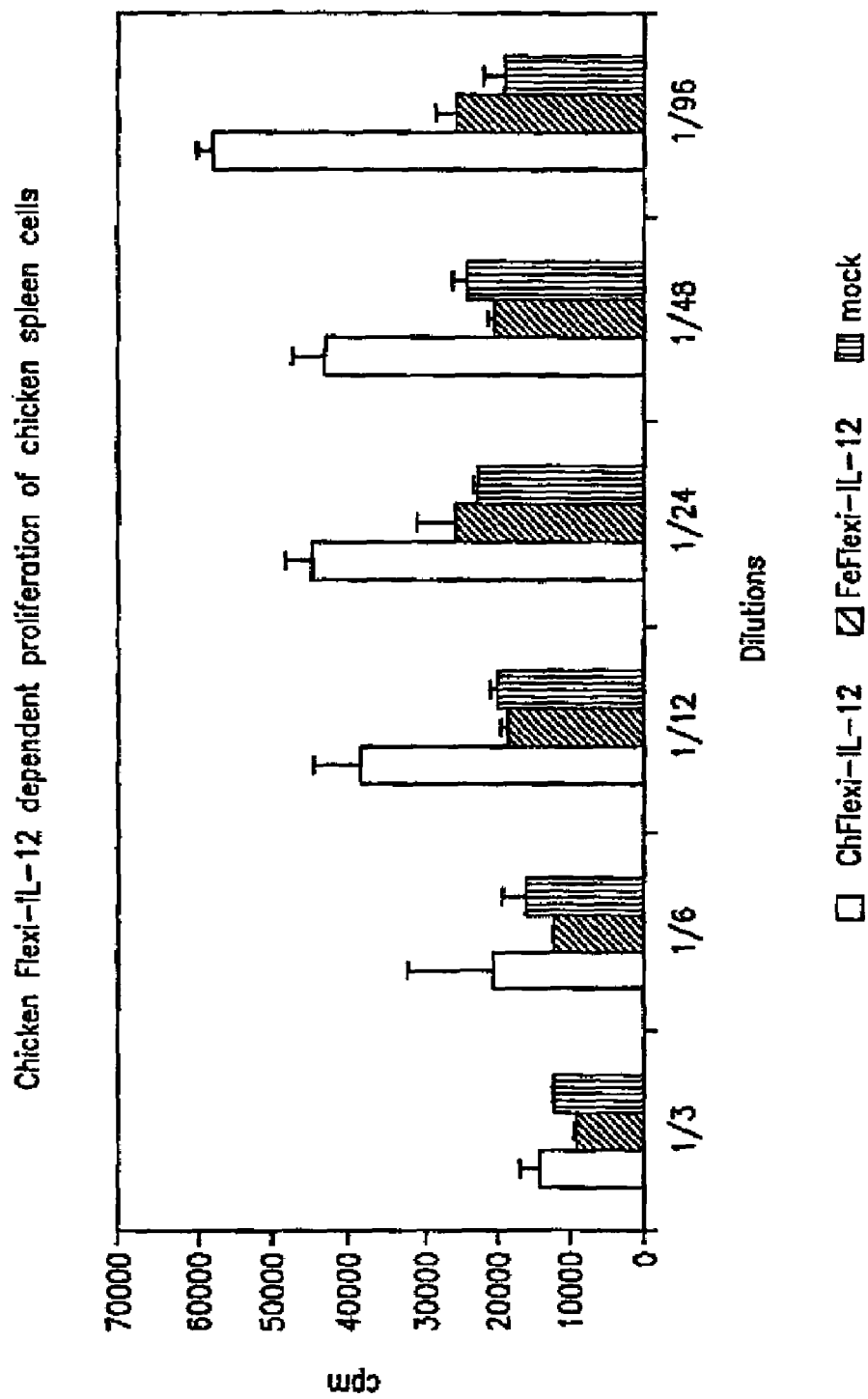
FIG. 12: Chicken Flexi-IL-12 dependent proliferation of chicken spleen cells (Fe=feline; mock=empty vector control).

After showing that co-transfection of single chain ChIL-12 p40 with single chain ChIL-12 p35 resulted in the formation of a bioactive ChIL-12 heterodimer (FIGS. 9 and 10), a single chain IL-12 molecule (ChFlexi-IL-12) was constructed. ChFlexi-IL-12 is a single chain p40-p35 heterodimeric construct in which the ChIL-12 p40 chain is linked to the ChIL-12 p35 chain by an in-frame $(Gly_4Ser)_3$-linker, also called a "hinge" region. By Western blot analysis it could be shown that the expression profile of the ChFlexi-IL-12 after transfection in COS-7 cells is comparable to that of FeFlexi-IL-12. Following incubation of freshly isolated chicken spleen cells with ChFlexi-IL-12 the release of both IFN-γ as well as cell proliferation were observed (FIG. 11 and FIG. 12). The results of these experiments prove that the chicken IL-12 flexi construct is also bioactive.

The invention claimed is:

1. An isolated protein comprising:

a subunit comprising an amino acid sequence showing at least 99% similarity with the amino acid sequence as depicted as SEQ ID NO: 1.

2. The protein according to claim 1, comprising a subunit having an apparent molecular weight of approximately 40 kD and having an amino acid sequence as depicted in SEQ ID NO: 1.

3. The protein according to claim 1, comprising
a subunit having an apparent molecular weight of approximately 40 kD and having an amino acid sequence as depicted in SEQ ID NO: 1 linked to another subunit with a molecular weight of approximately 35 kD).

4. An adjuvant composition comprising a protein according to claim 1, an adjuvant, and a pharmaceutically acceptable carrier.

* * * * *

UNITED STATES PATENT AND TRADEMARK OFFICE
CERTIFICATE OF CORRECTION

PATENT NO. : 7,347,996 B1  Page 1 of 1
APPLICATION NO. : 10/464630
DATED : March 25, 2008
INVENTOR(S) : Wilhelmus Gerardus Johannes Degen et al.

It is certified that error appears in the above-identified patent and that said Letters Patent is hereby corrected as shown below:

On the title page, item (75) Inventors: change from

"Wilhelmus Gerardus Johannes Degen, AS Doetinchem (NL); Virgil Elisabeth Joseph Caspar Schijns, KA Nijmegen (NL)"

to

--Wilhelmus Gerardus Johannes Degen, AS Doetinchem (NL); Virgil Elisabeth Joseph Caspar Schijns, KA Nijmegen (NL); Joan Burnside, Landenberg, PA (US)--

Signed and Sealed this

Eighth Day of December, 2009

David J. Kappos
*Director of the United States Patent and Trademark Office*